(12) United States Patent
Williams et al.

(10) Patent No.: US 7,833,156 B2
(45) Date of Patent: Nov. 16, 2010

(54) PROCEDURAL CANNULA AND SUPPORT SYSTEM FOR SURGICAL PROCEDURES

(75) Inventors: Michael S. Williams, Santa Rosa, CA (US); Richard S. Stack, Chapel Hill, NC (US); Geoffrey A. Orth, Sebastopol, CA (US); Jeffrey A. Smith, Petaluma, CA (US); Richard A. Glenn, Santa Rosa, CA (US); Daniel W. Fifer, Windsor, CA (US); William L. Athas, Chapel Hill, NC (US); Aurora Pryor, Durham, NC (US)

(73) Assignee: Transenterix, Inc., Morrisville, NC (US)

( * ) Notice: Subject to any disclaimer, the term of this patent is extended or adjusted under 35 U.S.C. 154(b) by 359 days.

(21) Appl. No.: 11/789,381

(22) Filed: Apr. 24, 2007

(65) Prior Publication Data

US 2008/0045803 A1 Feb. 21, 2008

Related U.S. Application Data

(60) Provisional application No. 60/794,563, filed on Apr. 24, 2006, provisional application No. 60/801,113, filed on May 17, 2006, provisional application No. 60/801,034, filed on May 17, 2006, provisional application No. 60/819,235, filed on Jul. 7, 2006.

(51) Int. Cl.
*A61B 1/00* (2006.01)
(52) U.S. Cl. ..................................... 600/184
(58) Field of Classification Search .................. 600/184
See application file for complete search history.

(56) References Cited

U.S. PATENT DOCUMENTS 3,561,432 A 2/1971 Yamaki et al.
3,896,793 A 7/1975 Mitsui
3,915,157 A 10/1975 Mitsui
4,112,932 A 9/1978 Chiulli
4,146,019 A 3/1979 Bass et al.
4,157,709 A 6/1979 Schuster et al.
4,245,624 A 1/1981 Komiya
4,407,273 A 10/1983 Ouchi (Continued)

FOREIGN PATENT DOCUMENTS

EP  1 586 275  12/2005

(Continued)

OTHER PUBLICATIONS

In re PCT Patent Application No. PCT/US2007/009936, "International Search Report and the Written Opinion of the International Searching Authority" 4 pages in length.

(Continued)

*Primary Examiner*—Todd E Manahan
*Assistant Examiner*—Naquan Ishman

(57) ABSTRACT

A system for performing minimally invasive medical procedures includes an elongate support advanceable into a body cavity. The elongate support supports a frame that carries a pair of tool cannulas, each of which has a lumen for receiving a tool useable to perform a procedure in the body cavity. The frame is expandable using pivotable frame members to orient the tool cannulas such that they allow the tools to be used in concert to carry out a procedure at a common location in the body cavity.

26 Claims, 25 Drawing Sheets

U.S. PATENT DOCUMENTS

| | | | |
|---|---|---|---|
| 4,436,087 A | 3/1984 | Ouchi | |
| 4,686,965 A | 8/1987 | Bonnet et al. | |
| 4,763,669 A | 8/1988 | Jaeger et al. | |
| 4,841,949 A | 6/1989 | Shimizu et al. | |
| 4,865,017 A | 9/1989 | Shinozuka | |
| 5,025,778 A | 6/1991 | Silverstein et al. | |
| 5,037,433 A | 8/1991 | Wilk et al. | |
| 5,099,827 A | 3/1992 | Melzer et al. | |
| 5,183,471 A | 2/1993 | Wilk | |
| 5,217,453 A | 6/1993 | Wilk | |
| 5,246,424 A | 9/1993 | Wilk | |
| 5,269,772 A | 12/1993 | Wilk | |
| 5,271,383 A | 12/1993 | Wilk | |
| 5,273,026 A | 12/1993 | Wilk | |
| 5,284,128 A | 2/1994 | Hart | |
| 5,297,536 A | 3/1994 | Wilk | |
| 5,312,391 A | 5/1994 | Wilk | |
| 5,318,013 A | 6/1994 | Wilk | 128/20 |
| 5,336,227 A | 8/1994 | Nakao et al. | |
| 5,347,989 A | 9/1994 | Monroe et al. | |
| 5,353,783 A | 10/1994 | Nakao et al. | |
| 5,368,015 A | 11/1994 | Wilk | |
| 5,373,840 A | 12/1994 | Knighton | |
| 5,386,818 A | 2/1995 | Schneebaum et al. | |
| 5,391,156 A | 2/1995 | Hildwein et al. | |
| 5,395,367 A | 3/1995 | Wilk | 606/1 |
| 5,400,770 A | 3/1995 | Nakao et al. | |
| 5,405,344 A | 4/1995 | Williamson et al. | |
| 5,417,697 A | 5/1995 | Wilk et al. | |
| 5,423,830 A | 6/1995 | Schneebaum et al. | |
| 5,441,507 A | 8/1995 | Wilk | |
| 5,454,827 A | 10/1995 | Aust et al. | |
| 5,458,131 A | 10/1995 | Wilk | |
| 5,486,182 A | 1/1996 | Nakao et al. | |
| 5,511,564 A | 4/1996 | Wilk | |
| 5,520,678 A | 5/1996 | Heckele et al. | |
| 5,601,588 A | 2/1997 | Tonomura et al. | |
| 5,609,563 A | 3/1997 | Suzuki et al. | |
| 5,624,380 A | 4/1997 | Takayama et al. | |
| 5,645,519 A | 7/1997 | Lee et al. | |
| 5,653,705 A | 8/1997 | de la Torre et al. | |
| 5,702,408 A | 12/1997 | Wales et al. | |
| 5,779,646 A | 7/1998 | Koblish et al. | |
| 5,817,061 A | 10/1998 | Goodwin et al. | |
| 5,876,325 A | 3/1999 | Mizuno et al. | |
| 5,916,147 A | 6/1999 | Boury | |
| 5,951,466 A | 9/1999 | Segermark et al. | |
| 5,957,913 A | 9/1999 | de la Torre et al. | |
| 6,033,426 A | 3/2000 | Kaji | |
| 6,066,090 A | 5/2000 | Yoon | |
| 6,085,749 A | 7/2000 | Wardle et al. | |
| 6,099,506 A | 8/2000 | Macoviak et al. | |
| 6,117,158 A | 9/2000 | Measamer et al. | |
| 6,120,433 A | 9/2000 | Mizuno et al. | |
| 6,159,200 A | 12/2000 | Verdura et al. | |
| 6,168,607 B1 | 1/2001 | Wattiez et al. | |
| 6,210,397 B1 | 4/2001 | Aboul-Hosn et al. | |
| 6,217,555 B1 | 4/2001 | Hart et al. | |
| 6,234,958 B1 | 5/2001 | Snoke et al. | |
| 6,254,534 B1 | 7/2001 | Butler et al. | |
| 6,315,770 B1 | 11/2001 | de la Torre et al. | |
| 6,352,503 B1 * | 3/2002 | Matsui et al. | 600/104 |
| 6,440,061 B1 | 8/2002 | Wenner et al. | |
| 6,454,783 B1 | 9/2002 | Piskun | |
| 6,458,074 B1 | 10/2002 | Matsui et al. | |
| 6,468,203 B2 | 10/2002 | Belson | |
| 6,488,620 B1 | 12/2002 | Segermark et al. | |
| 6,527,753 B2 | 3/2003 | Sekine et al. | |
| 6,569,105 B1 | 5/2003 | Kortenbach et al. | |
| 6,582,364 B2 | 6/2003 | Butler et al. | |
| 6,610,007 B2 | 8/2003 | Belson et al. | |
| 6,669,674 B1 | 12/2003 | Macoviak et al. | |
| 6,706,050 B1 | 3/2004 | Giannadakis | |
| 6,783,491 B2 | 8/2004 | Saadat et al. | |
| 6,800,056 B2 | 10/2004 | Tartaglia et al. | |
| 6,811,532 B2 | 11/2004 | Ogura et al. | |
| 6,837,846 B2 | 1/2005 | Jaffe et al. | |
| 6,837,849 B2 | 1/2005 | Ogura et al. | |
| 6,840,951 B2 | 1/2005 | de la Torre et al. | |
| 6,846,287 B2 | 1/2005 | Bonadio et al. | |
| 6,858,005 B2 | 2/2005 | Ohline et al. | |
| 6,869,396 B2 | 3/2005 | Belson | |
| 6,890,297 B2 | 5/2005 | Belson | |
| 6,939,296 B2 | 9/2005 | Ewers et al. | |
| 6,958,037 B2 | 10/2005 | Ewers et al. | |
| 6,974,411 B2 | 12/2005 | Belson | |
| 6,984,203 B2 | 1/2006 | Tartaglia et al. | |
| 7,039,425 B1 | 5/2006 | Nakao | |
| 7,052,454 B2 | 5/2006 | Taylor | |
| 7,081,089 B2 | 7/2006 | Bonadio et al. | |
| 7,090,637 B2 | 8/2006 | Danitz et al. | |
| 7,147,650 B2 | 12/2006 | Lee | |
| 7,182,752 B2 | 2/2007 | Stubbs et al. | |
| 7,285,112 B2 | 10/2007 | Stubbs et al. | |
| 7,300,399 B2 | 11/2007 | Bonadio et al. | |
| 7,316,699 B2 | 1/2008 | McFarlane | |
| 7,338,473 B2 | 3/2008 | Campbell et al. | |
| 7,338,513 B2 | 3/2008 | Lee et al. | |
| 7,344,547 B2 | 3/2008 | Piskun | |
| 7,347,863 B2 | 3/2008 | Rothe et al. | |
| 7,361,180 B2 | 4/2008 | Saadat et al. | |
| 7,364,582 B2 | 4/2008 | Lee | |
| 7,390,329 B2 | 6/2008 | Westra et al. | |
| 7,410,483 B2 | 8/2008 | Danitz et al. | |
| 7,491,165 B2 | 2/2009 | Kogasaka et al. | |
| 7,615,066 B2 | 11/2009 | Danitz et al. | |
| 7,637,905 B2 | 12/2009 | Saadat et al. | |
| 2001/0049497 A1 * | 12/2001 | Kalloo et al. | 604/164.01 |
| 2003/0045778 A1 | 3/2003 | Ohline et al. | |
| 2003/0216619 A1 | 11/2003 | Scirica et al. | |
| 2003/0233025 A1 | 12/2003 | Saadat et al. | |
| 2003/0233026 A1 | 12/2003 | Saadat et al. | |
| 2003/0233027 A1 | 12/2003 | Ewers et al. | |
| 2003/0233056 A1 | 12/2003 | Saadat et al. | |
| 2003/0233057 A1 | 12/2003 | Saadat et al. | |
| 2003/0233058 A1 | 12/2003 | Ewers et al. | |
| 2003/0233066 A1 | 12/2003 | Ewers et al. | |
| 2003/0236505 A1 | 12/2003 | Bonadio et al. | |
| 2004/0138525 A1 * | 7/2004 | Saadat et al. | 600/104 |
| 2004/0138529 A1 | 7/2004 | Wiltshire et al. | |
| 2004/0162568 A1 | 8/2004 | Saadat et al. | |
| 2004/0186350 A1 | 9/2004 | Brenneman et al. | |
| 2004/0249367 A1 | 12/2004 | Saadat et al. | |
| 2005/0065397 A1 | 3/2005 | Saadat et al. | |
| 2005/0065401 A1 | 3/2005 | Saadat et al. | |
| 2005/0107663 A1 | 5/2005 | Saadat et al. | |
| 2005/0107667 A1 | 5/2005 | Danitz et al. | |
| 2005/0113640 A1 | 5/2005 | Saadat et al. | |
| 2005/0137454 A1 | 6/2005 | Saadat et al. | |
| 2005/0137455 A1 | 6/2005 | Ewers | |
| 2005/0137456 A1 | 6/2005 | Saadat et al. | |
| 2005/0165272 A1 | 7/2005 | Okada et al. | |
| 2005/0222495 A1 | 10/2005 | Okada et al. | |
| 2005/0228224 A1 | 10/2005 | Okada et al. | |
| 2005/0234294 A1 | 10/2005 | Saadat et al. | |
| 2005/0234296 A1 | 10/2005 | Saadat et al. | |
| 2005/0250990 A1 | 11/2005 | Le et al. | |
| 2005/0251091 A1 | 11/2005 | Saadat et al. | |
| 2005/0251176 A1 | 11/2005 | Swanstrom et al. | |
| 2005/0251177 A1 | 11/2005 | Saadat et al. | |
| 2005/0267335 A1 | 12/2005 | Okada et al. | |
| 2005/0272977 A1 | 12/2005 | Saadat et al. | |
| 2005/0273084 A1 | 12/2005 | Hinman | |
| 2005/0273085 A1 | 12/2005 | Hinman | |

| | | |
|---|---|---|
| 2005/0277945 A1 | 12/2005 | Saadat et al. |
| 2005/0277975 A1 | 12/2005 | Saadat et al. |
| 2005/0288551 A1 | 12/2005 | Callister et al. |
| 2006/0020241 A1 | 1/2006 | Piskun et al. |
| 2006/0020287 A1 | 1/2006 | Lee et al. |
| 2006/0025652 A1 | 2/2006 | Vargas |
| 2006/0030755 A1 | 2/2006 | Ewers et al. |
| 2006/0036267 A1 | 2/2006 | Saadat et al. |
| 2006/0058582 A1 | 3/2006 | Maahs et al. |
| 2006/0111209 A1 | 5/2006 | Hinman et al. |
| 2006/0111210 A1 | 5/2006 | Hinman |
| 2006/0111615 A1 | 5/2006 | Danitz et al. |
| 2006/0111616 A1 | 5/2006 | Danitz |
| 2006/0161185 A1 | 7/2006 | Saadat et al. |
| 2006/0167416 A1 | 7/2006 | Mathis et al. |
| 2006/0178560 A1 | 8/2006 | Saadat et al. |
| 2006/0178562 A1 | 8/2006 | Saadat et al. |
| 2006/0183975 A1 | 8/2006 | Saadat et al. |
| 2006/0184161 A1 | 8/2006 | Maahs et al. |
| 2006/0189845 A1 | 8/2006 | Maahs et al. |
| 2006/0224174 A1 | 10/2006 | Smith et al. |
| 2006/0237022 A1 | 10/2006 | Chen et al. |
| 2006/0247500 A1 | 11/2006 | Voegele et al. |
| 2006/0258909 A1 | 11/2006 | Saadat et al. |
| 2007/0021737 A1 | 1/2007 | Lee |
| 2007/0049966 A1 | 3/2007 | Bonadio et al. |
| 2007/0093695 A1 | 4/2007 | Bonadio et al. |
| 2007/0123840 A1 | 5/2007 | Cox |
| 2007/0151390 A1* | 7/2007 | Blumenkranz et al. ... 74/490.06 |
| 2007/0167679 A1 | 7/2007 | Miyamoto et al. |
| 2007/0167680 A1 | 7/2007 | Miyamoto et al. |
| 2007/0221700 A1 | 9/2007 | Ortiz et al. |
| 2007/0221701 A1 | 9/2007 | Ortiz et al. |
| 2007/0225562 A1 | 9/2007 | Ortiz et al. |
| 2007/0255219 A1 | 11/2007 | Vaugh et al. |
| 2007/0276430 A1 | 11/2007 | Lee et al. |
| 2007/0283970 A1 | 12/2007 | Mohr et al. |
| 2007/0287884 A1 | 12/2007 | Schena et al. |
| 2007/0287889 A1 | 12/2007 | Mohr |
| 2007/0287992 A1 | 12/2007 | Diolaiti et al. |
| 2007/0299387 A1 | 12/2007 | Williams et al. |
| 2008/0027476 A1 | 1/2008 | Piskun |
| 2008/0051631 A1 | 2/2008 | Dejima et al. |
| 2008/0058595 A1 | 3/2008 | Snoke et al. |
| 2008/0064921 A1 | 3/2008 | Larkin et al. |
| 2008/0064927 A1 | 3/2008 | Larkin et al. |
| 2008/0064931 A1 | 3/2008 | Schena et al. |
| 2008/0065097 A1 | 3/2008 | Duval et al. |
| 2008/0065098 A1 | 3/2008 | Larkin |
| 2008/0065099 A1 | 3/2008 | Cooper et al. |
| 2008/0065100 A1 | 3/2008 | Larkin |
| 2008/0065101 A1 | 3/2008 | Larkin |
| 2008/0065102 A1 | 3/2008 | Cooper |
| 2008/0065103 A1 | 3/2008 | Cooper et al. |
| 2008/0065104 A1 | 3/2008 | Larkin et al. |
| 2008/0065105 A1 | 3/2008 | Larkin et al. |
| 2008/0065106 A1 | 3/2008 | Larkin |
| 2008/0065107 A1 | 3/2008 | Larkin et al. |
| 2008/0065108 A1 | 3/2008 | Diolaiti |
| 2008/0065109 A1 | 3/2008 | Larkin |
| 2008/0065110 A1 | 3/2008 | Duval et al. |
| 2008/0071288 A1 | 3/2008 | Larkin et al. |
| 2008/0071289 A1 | 3/2008 | Cooper et al. |
| 2008/0071290 A1 | 3/2008 | Larkin et al. |
| 2008/0071291 A1 | 3/2008 | Duval et al. |
| 2008/0086167 A1 | 4/2008 | Mastri et al. |
| 2008/0091170 A1 | 4/2008 | Vargas et al. |
| 2008/0183035 A1 | 7/2008 | Vakharia et al. |
| 2008/0188868 A1 | 8/2008 | Weitzner et al. |
| 2008/0188869 A1 | 8/2008 | Weitzner et al. |
| 2008/0188890 A1 | 8/2008 | Weitzner et al. |
| 2008/0221391 A1 | 9/2008 | Weitzner et al. |
| 2008/0243176 A1 | 10/2008 | Weitzner et al. |
| 2008/0255420 A1 | 10/2008 | Lee et al. |
| 2008/0255519 A1 | 10/2008 | Piskun et al. |
| 2008/0262294 A1 | 10/2008 | Ewers et al. |
| 2008/0262300 A1 | 10/2008 | Ewers et al. |
| 2008/0262525 A1 | 10/2008 | Chang et al. |
| 2008/0262539 A1 | 10/2008 | Ewers et al. |
| 2008/0275297 A1 | 11/2008 | Bakos et al. |
| 2008/0287862 A1 | 11/2008 | Weitzner et al. |
| 2009/0023985 A1 | 1/2009 | Ewers |
| 2009/0171161 A1 | 7/2009 | Ewers et al. |
| 2009/0227843 A1 | 9/2009 | Smith et al. |

FOREIGN PATENT DOCUMENTS

| | | |
|---|---|---|
| EP | 1 586 275 A3 | 12/2005 |
| JP | 54-136780 | 10/1979 |
| JP | 5-184534 | 7/1993 |
| JP | 8117238 | 5/1996 |
| JP | 9-262239 | 10/1997 |
| WO | WO 96/04875 | 2/1996 |
| WO | WO 97/42889 A1 | 11/1997 |
| WO | WO 2005/009227 A1 | 2/2005 |
| WO | WO 2005/058239 A2 | 6/2005 |
| WO | WO 2006/019723 A2 | 2/2006 |
| WO | WO 2006/113216 A2 | 10/2006 |
| WO | WO 2007/146987 A2 | 12/2007 |

OTHER PUBLICATIONS

In re PCT Patent Application No. PCT/US2007/009936, "International Preliminary Report on Patentability" and "Written Opinion of the International Searching Authority" 7 pages in length.
U.S. Appl. No. 60/813030, Larkin.
U.S. Appl. No. 60/813126, Cooper.
U.S. Appl. No. 60/813028, Cooper.
U.S. Appl. No. 60/813129, Cooper.
U.S. Appl. No. 60/813173, Larkin.
U.S. Appl. No. 60/813131, Duval.
U.S. Appl. No. 60/813172, Cooper.
U.S. Appl. No. 60/813198, Larkin.
U.S. Appl. No. 60/813207, Diolaiti.
U.S. Appl. No. 60/813029, Larkin.
U.S. Appl. No. 60/813125, Larkin.
U.S. Appl. No. 60/813075, Larkin.
U.S. Appl. No. 60/813328, Mohr.

* cited by examiner

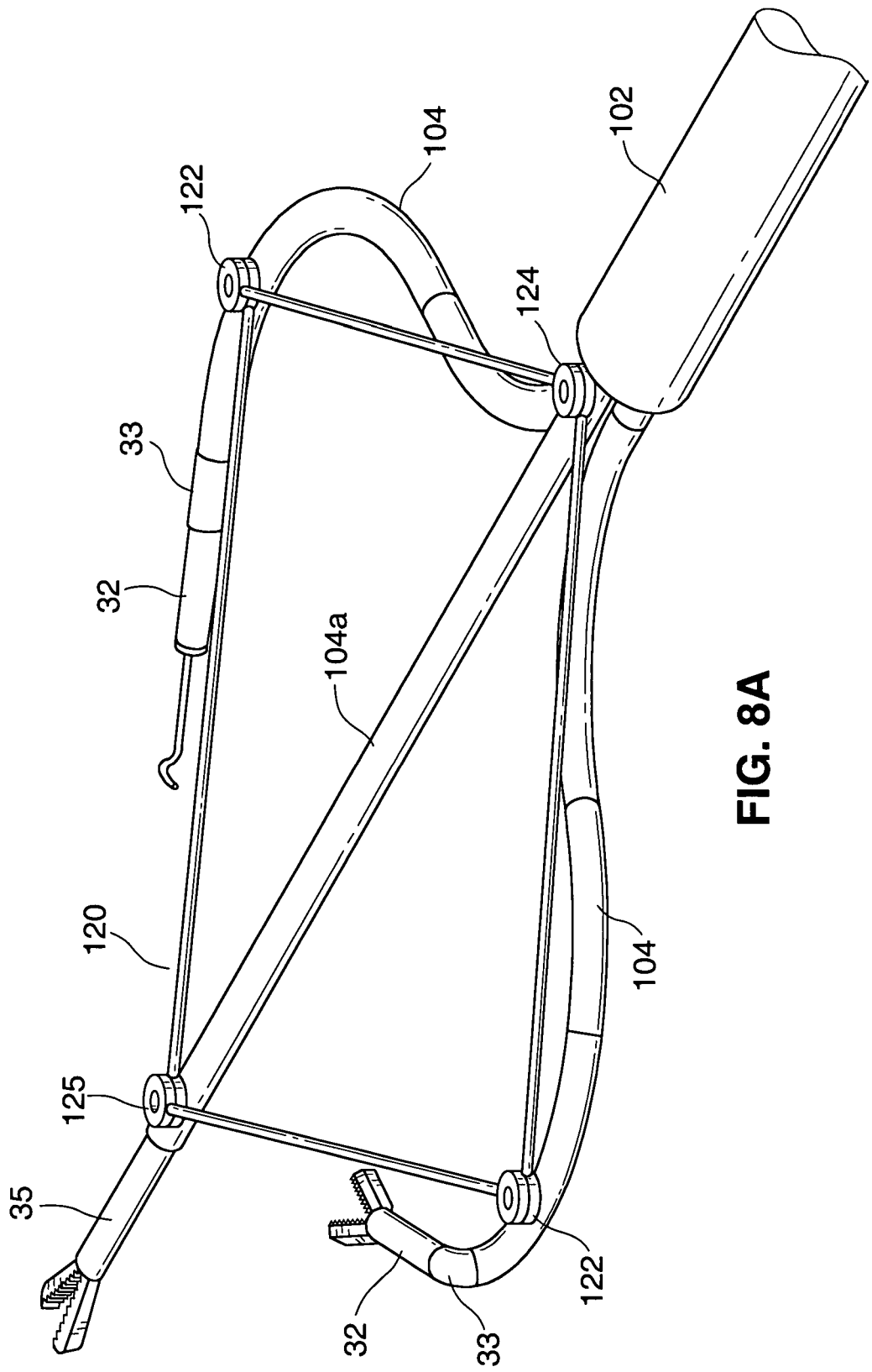

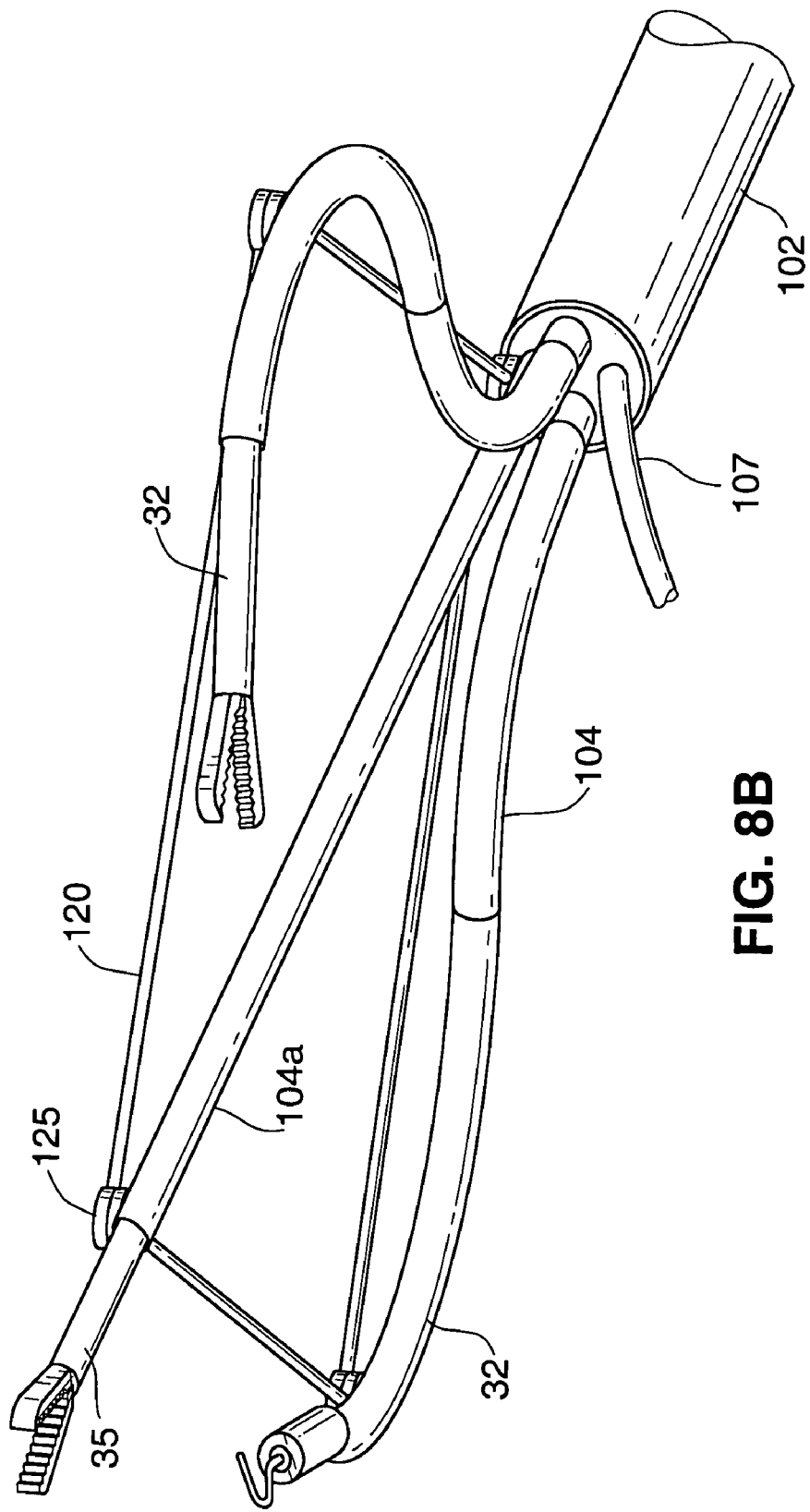

_US 7,833,156 B2_

PROCEDURAL CANNULA AND SUPPORT SYSTEM FOR SURGICAL PROCEDURES

RELATED APPLICATIONS

This application claims the benefit of U.S. Provisional Application No. 60/794,563, filed Apr. 24, 2006, U.S. Provisional Application No. 60/801,113, filed May 17, 2006, U.S. Provisional Application No. 60/801,034, May 17, 2006, and U.S. Provisional Application No. 60/819,235, filed Jul. 7, 2006.

FIELD OF THE INVENTION

The present invention relates to the field of devices and procedures for use in performing surgery in the peritoneal cavity using access through a natural orifice.

BACKGROUND OF THE INVENTION

Surgery in the abdominal cavity is typically performed using open surgical techniques or laparoscopic procedures. Each of these procedures requires incisions through the skin and underlying muscle and peritoneal tissue, and thus results in the potential for post-surgical scarring and/or hernias.

Systems and techniques in which access to the abdominal cavity is gained through a natural orifice are advantageous in that incisions through the skin and underlying muscle and peritoneal tissue may be avoided. Use of such systems can provide access to the peritoneal cavity using an access device inserted into the esophagus, stomach or intestine (via, for example, the mouth or rectum). Instruments are then advanced through the access device into the peritoneal cavity via an incision in the wall of the esophagus, stomach or intestine. Other forms of natural orifice access, such as vaginal access, may similarly be used.

BRIEF DESCRIPTION OF THE DRAWINGS

FIGS. 8A and 8B are a top perspective view and a bottom perspective view, respectively, of a distal end of the system of FIG. 3 using an additional tool cannula.

In FIG. 11C, the center retractor is shown in a downwardly deflected position, and phantom lines are shown to illustrate the retractor in an upwardly deflected position.

DETAILED DESCRIPTION OF THE DRAWINGS

Figure 1:
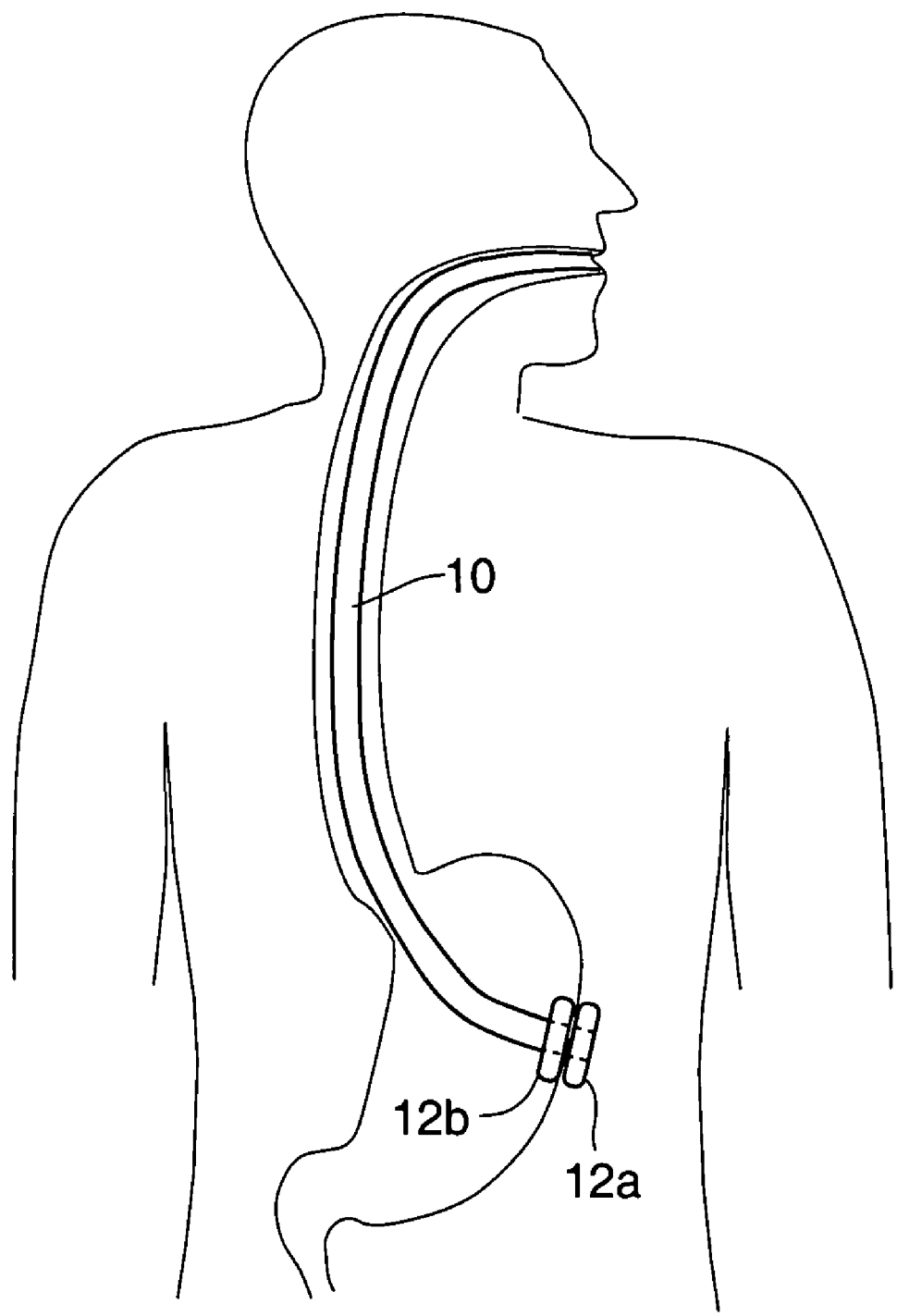
FIG. 1 is a perspective view of an access cannula anchored in an incision in a stomach for use in a natural orifice procedure.

Applicant's prior Provisional Application No. U.S. application Ser. No. 11/528,009, TRANSGASTRIC SURGICAL DEVICES AND PROCEDURES, Filed Sep. 27, 2006 describes various embodiments of surgical access cannulas for use in gaining access to the peritoneal cavity of a patient via a natural orifice. When used for transoral procedures, the distal end of an access cannula 10 (FIG. 1) is advanced orally through the esophagus and into the stomach or intestine. Instruments are passed through the cannula and are used to form an incision in the stomach or intestinal wall, giving access to the peritoneal cavity. The access cannula 10 is anchored in the incision using expandable anchors 12a, 12b positioned against the inner and outer surfaces of the stomach wall. Insufflation gas may be introduced into the peritoneal cavity via the access cannula to create working space within the cavity. The access cannula may include valves or seals that allow for sealed access through the incision, permitting sterile passage of instruments into the peritoneal cavity without loss of insufflation pressure. The access cannula 10 may be a flexible tube formed of polymeric material (e.g. polyurethane) having an embedded braid. In other embodiments, a more rigid access cannula may be used. The '009 application, which is incorporated herein by reference, describes various additional components of access cannula systems, including anchoring features, elements for forming incisions in an interior body wall such as the stomach, and closure devices.

This application describes a procedural cannula and support system ideally used in combination with an access cannula that has been used to gain access to the peritoneal cavity. For example, once access cannula 10 has been passed through the oral cavity and stomach and secured within a stomach wall incision using anchors 12a, 12b, a procedural cannula and support system of the type described herein is passed through the access cannula and into the peritoneal cavity.

For certain procedures, it would be advantageous to allow the surgeon to perform a natural orifice surgical procedure in a manner that allows him/her to approach the surgical target within the peritoneal cavity from the same direction from which s/he would typically approach that same structure using a laparoscopic or open surgical procedure. For example, if a particular procedure utilizes an anterior approach to the treatment site when carried out using laparoscopic or surgical techniques, it would also be desirable to allow the surgeon to approach the treatment site from an anterior perspective even when using a natural orifice technique. The system illustrated in the attached drawings allows these same approaches to be used using natural orifice access, thus allowing a surgeon to easily and intuitively transition between natural orifice surgical procedures and open or laparoscopic procedures.

In general, the disclosed embodiments include at least one procedural or tool cannula through which instruments are passed to the operative site. A support system provides rigid support for the procedural cannula(s) within the body.

Figure 2A:
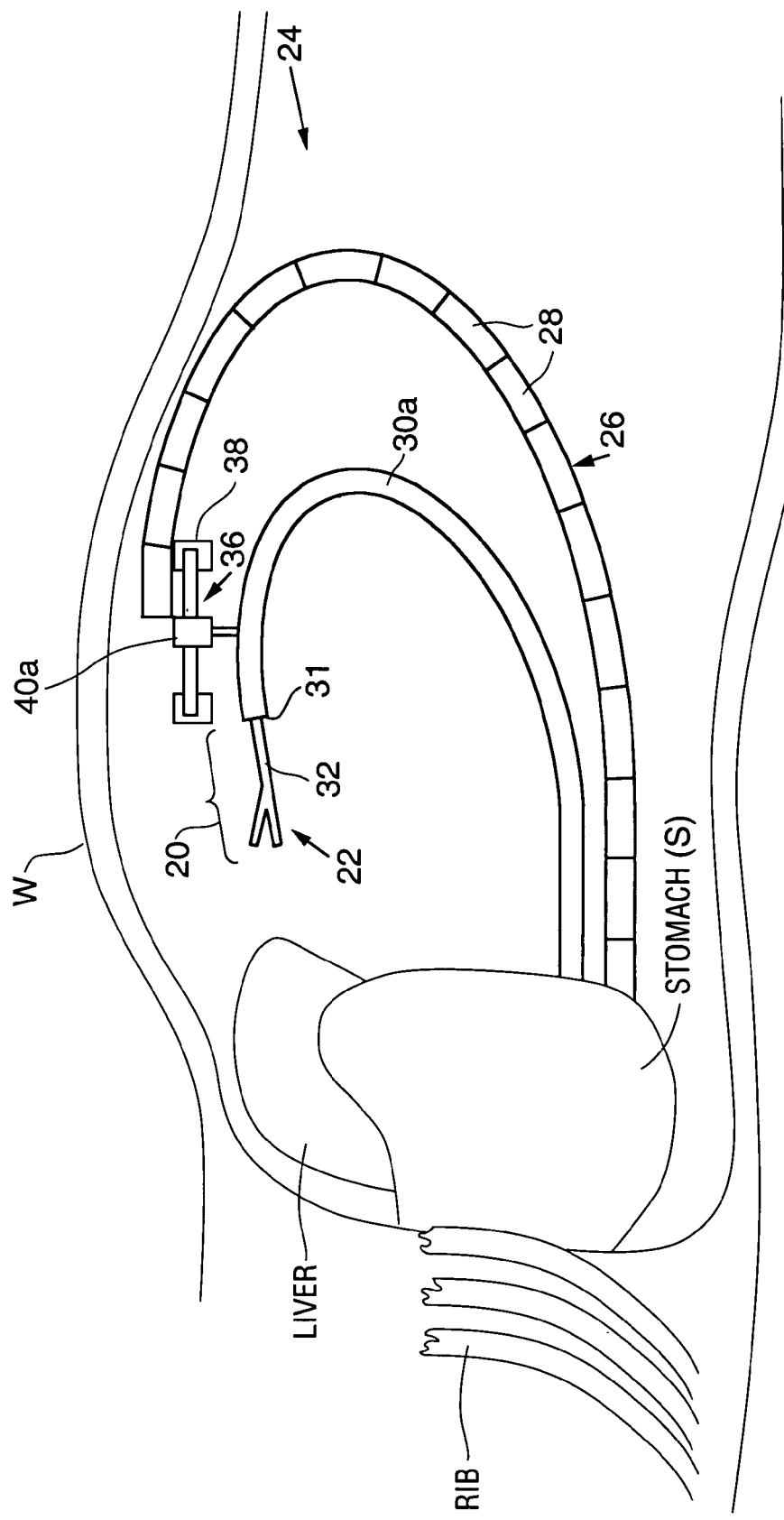
FIG. 2A is a schematic side view showing the interior of an abdominal cavity, and further showing use of a first embodiment of a procedural cannula and support system.
Figure 2B:
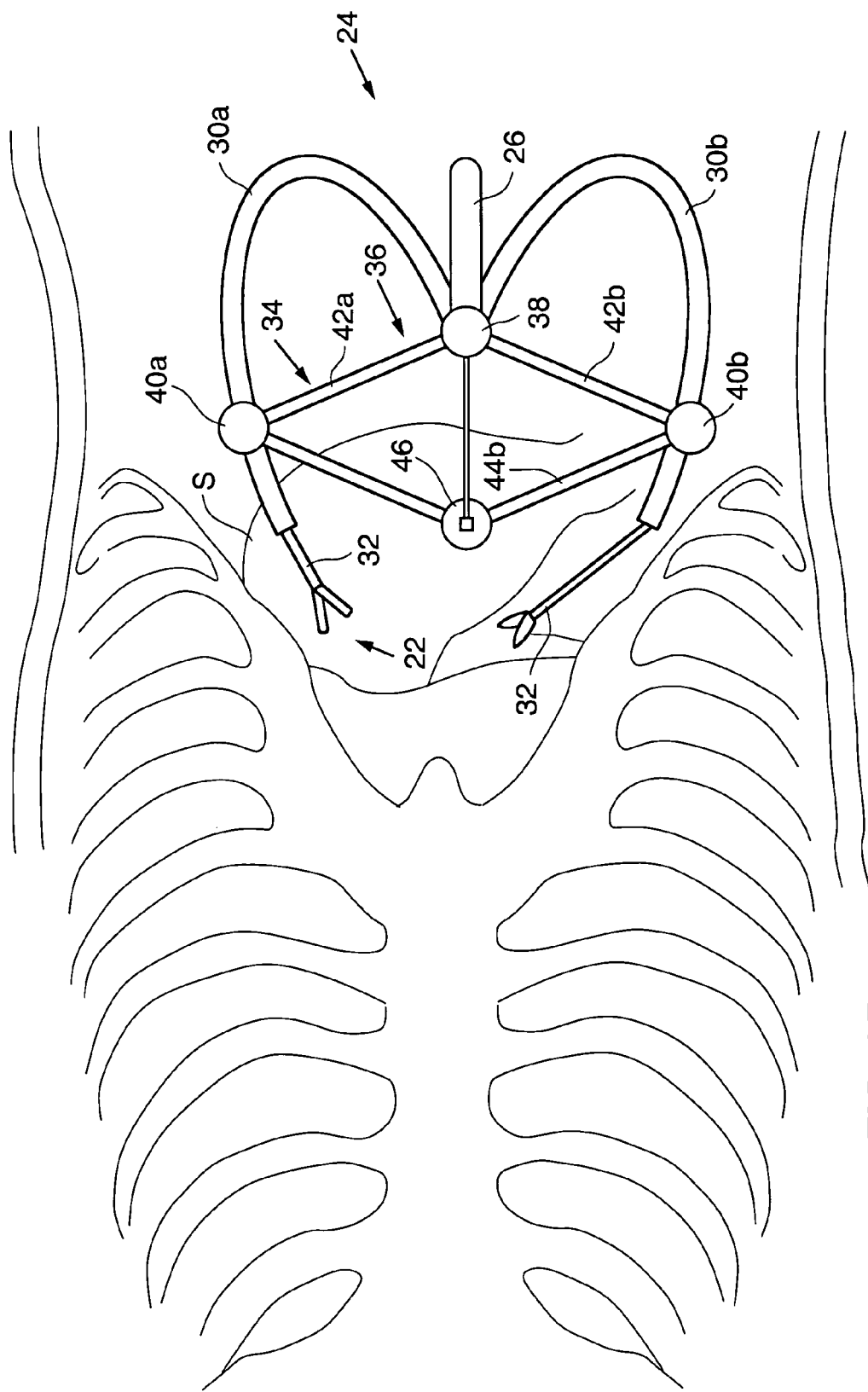
FIG. 2B is a schematic top view (anterior view) showing the interior of an abdominal cavity and further illustrating use of the procedural cannula and support system of FIG. 2A.

Referring to FIGS. 2A and 2B, one embodiment of a natural orifice surgical system includes an instrument system 22 and a support system 24. These figures schematically illustrate the peritoneal cavity of a patient with the support system and instrument system extending into the cavity from an incision (not shown) through the stomach wall. In use, the support system 24 forms a sort of scaffold within the body to support the instrument system 22 in a location that allows the surgeon to advance the instruments of the instrument system using a desired approach. Thus, for example, if performing a procedure that typically uses an anterior approach when carried out surgically or laparoscopically, the user might position the support system 24 adjacent the abdominal wall W as shown in FIG. 2A.

Support system 24 includes an elongate shaft or spine 26 that extends from an incision in a body organ such as the stomach S or other hollow organ (e.g. intestine, vagina) from which natural orifice access has been gained as described above. In a preferred embodiment, shaft 26 is disposed within an access cannula 10 which may be of the type shown in FIG. 1. Shaft 26 is preferably one capable of being sufficiently flexible for passage through the natural orifice and body organ, and for manipulation within the peritoneal space, but also capable of being placed in a self-supporting rigid state once positioned at a desired location. In one embodiment, shaft 26 is a shaft formed of a plurality of spine elements 28 having tensioning cables that may be placed under tension to stiffen the shaft 26. As will be discussed in greater detail below, the spine elements are shaped such that the shaft 26 will assume a shape predetermined to give the curvature needed to position the shaft 26 at the desired location. Shaft 26 may include a lumen (not shown) or other features for supporting an endoscope (not shown) oriented towards the treatment site.

Instrument system 22 includes one or more procedural cannulas 30a, 30b, each having an opening 152 at or near its distal end. Cannulas 30a, 30b may include a curved distal portion as shown, and may additionally or alternatively be deflectable in predetermined directions using pullwires, mandrels, or other deflection mechanisms, including those known in the art for deflecting catheters, introducers and guidewires.

Instruments 32 (e.g. forceps, endoscopes, suture devices, staplers) are extendable through the procedural cannulas 30a, 30b and into position at the target site in the peritoneal cavity. As best shown in FIG. 2B, two procedural cannulas are useful in that they allow for the simultaneous use of two instruments 32. The procedural cannulas 30a, 30b may be passed into the peritoneal cavity via the same access cannula 10 (FIG. 1) through which the support shaft 26 extends, or they may be passed through one or more separately placed access cannulas 10, or, as described in detail in connection with FIG. 3, they may be passed through a lumen in the shaft 26.

A coupling 34 couples the instrument system 22 and support system 24. The coupling 24 may by any type of device that couples the procedural cannulas 30a, 30b to the shaft 28. In the FIG. 2A-2B embodiment, the coupling takes the form of a linkage 36 that allows the cannulas to be suspended from the shaft 26 and also provides the additional benefit of maintaining the orientation of the cannulas 30a, 30b relative to one another. The linkage 36, which is most visible in FIG. 2B, includes a first mount 38 on the shaft 26, and second mounts 40a, 40b on the procedural cannulas 30a, 30b. Linkage bars 42a, 42b are pivotally coupled to the mount 38 and the mounts 40a, 40b. Second linkage bars 44a, 44b are pivotally coupled to the mounts 40a, 40b and a pivot point 46. As can be seen in FIGS. 2A and 2B, the support system 24 positions the procedural cannulas 30a, 30b so that access to the treatment site can be gained using an approach that is familiar to the practitioner, despite the fact that the instruments are inserted into the body using a drastically different approach. Deflection features of the cannulas 30a, 30b allow those cannulas to be manipulated so as to position the instruments 32 where they are needed, without requiring that the instruments include specialized features for steering and deflection. The linkage 36 maintains the relative orientation of the cannulas 30a, 30b towards the treatment site.

Figure 3:
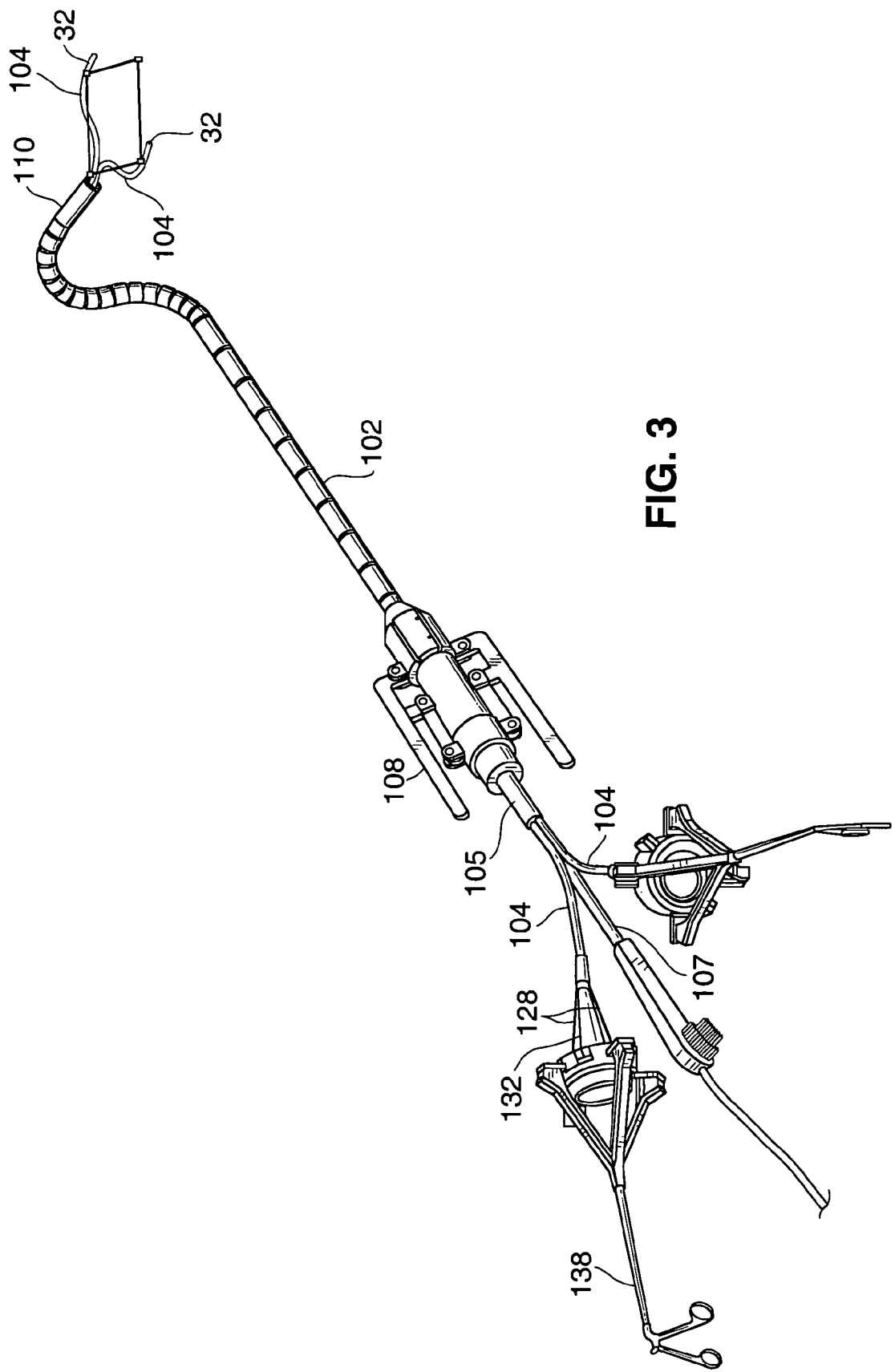
FIG. 3 is a perspective view showing an alternative procedural cannula and support system.

FIG. 3 shows a second embodiment of a natural orifice surgical system 100. System 100 includes a locking spine 102 and a pair of tool cannulas 104. The system 100 is similar to the embodiment of FIGS. 2A and 2B, but differs in that the tool cannulas 104 pass through a lumen 105 in the shaft of the locking spine 102 of the support system, allowing for a more streamlined system that occupies a reduced amount of space. An endoscope 107 also extends through the spine 102, allowing the user to observe the procedure being carried out at the distal end of the system. Instruments 32 extend from the tool cannulas to the operative sites. Instruments 32 may include forceps, retractors or any other instruments needed to carry out the desired procedure within the peritoneum.

Figure 9:
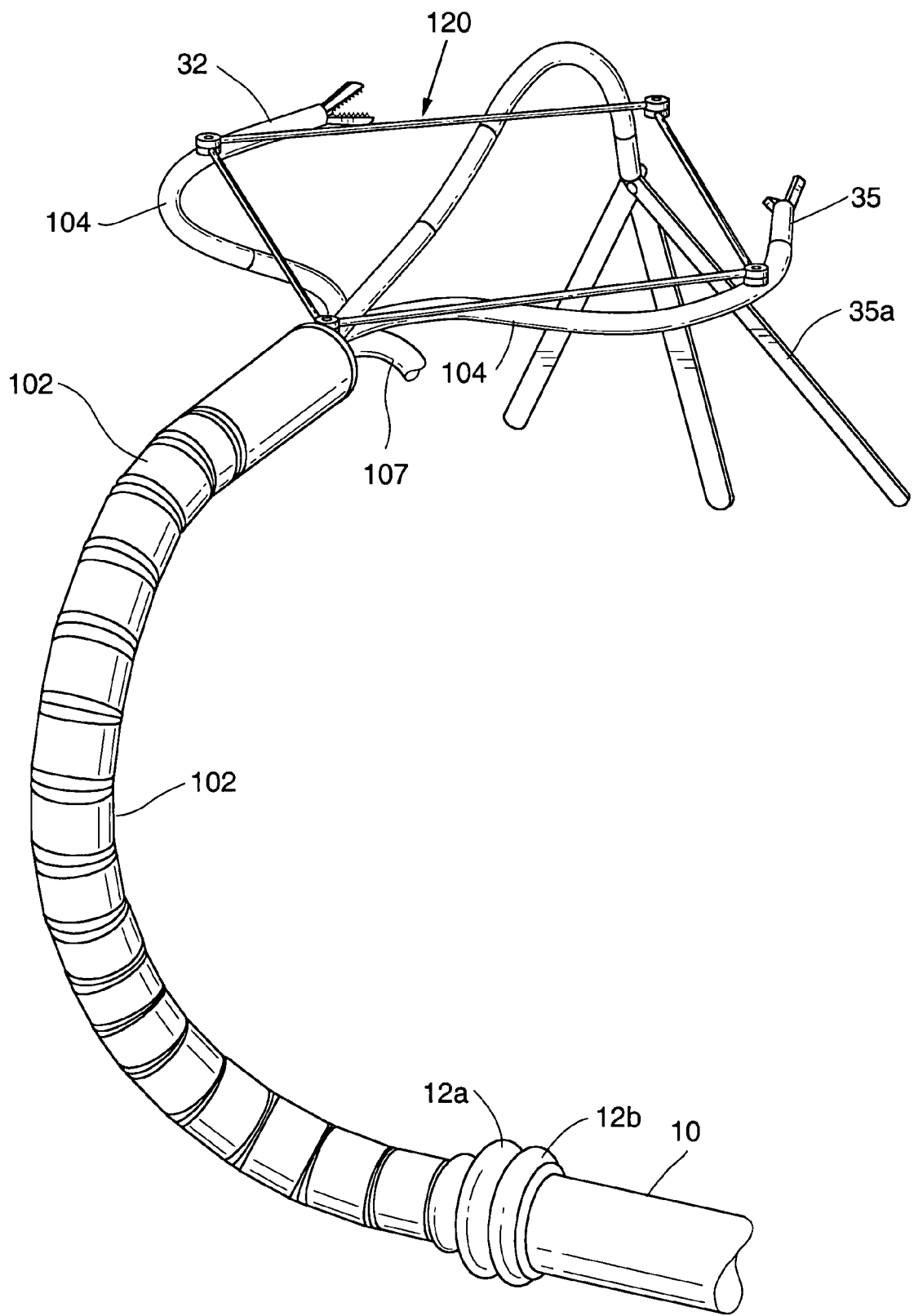
FIGS. 9 and 10 are perspective views of the system of FIG. 3 extending from an access cannula and including a retractor extending from a longitudinal tool cannula.
Figure 10:
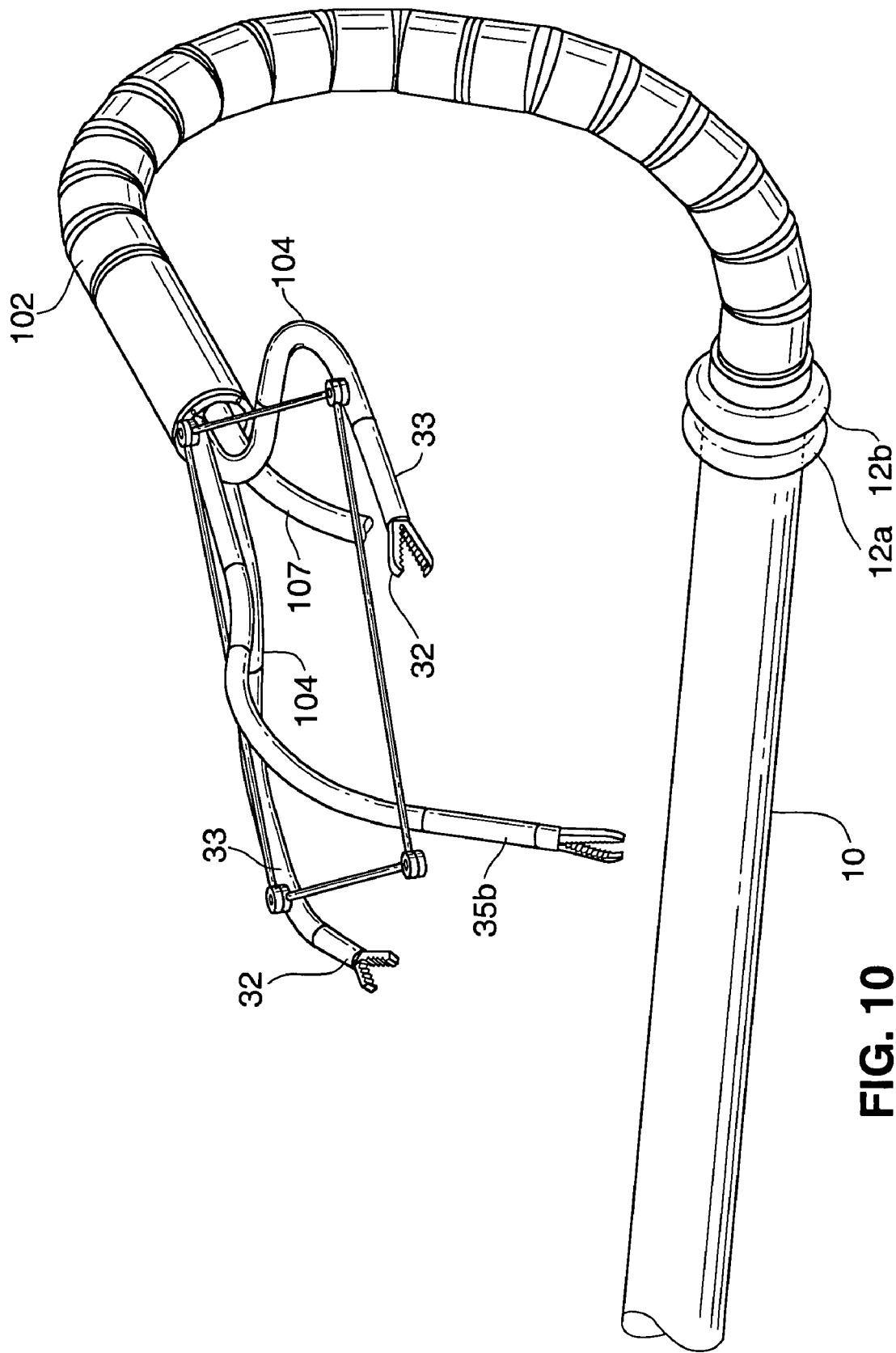

The locking spine 102 is preferably passed into the body through an access cannula 10 as described in connection with FIG. 1 and as shown in FIGS. 9 and 10.

Spine 102 is preferably one capable of being sufficiently flexible for manipulation within the peritoneal space, but also capable of being placed in a self-supporting rigid state once positioned at a desired location. In one embodiment, spine 102 is a shaft formed of a plurality of spine elements having tensioning cables that may be placed under tension to stiffen the shaft. The spine elements are shaped such that the spine will assume a shape predetermined to give the curvature needed to position the distal end of the spine at the desired location and oriented towards the treatment site.

Figure 4:
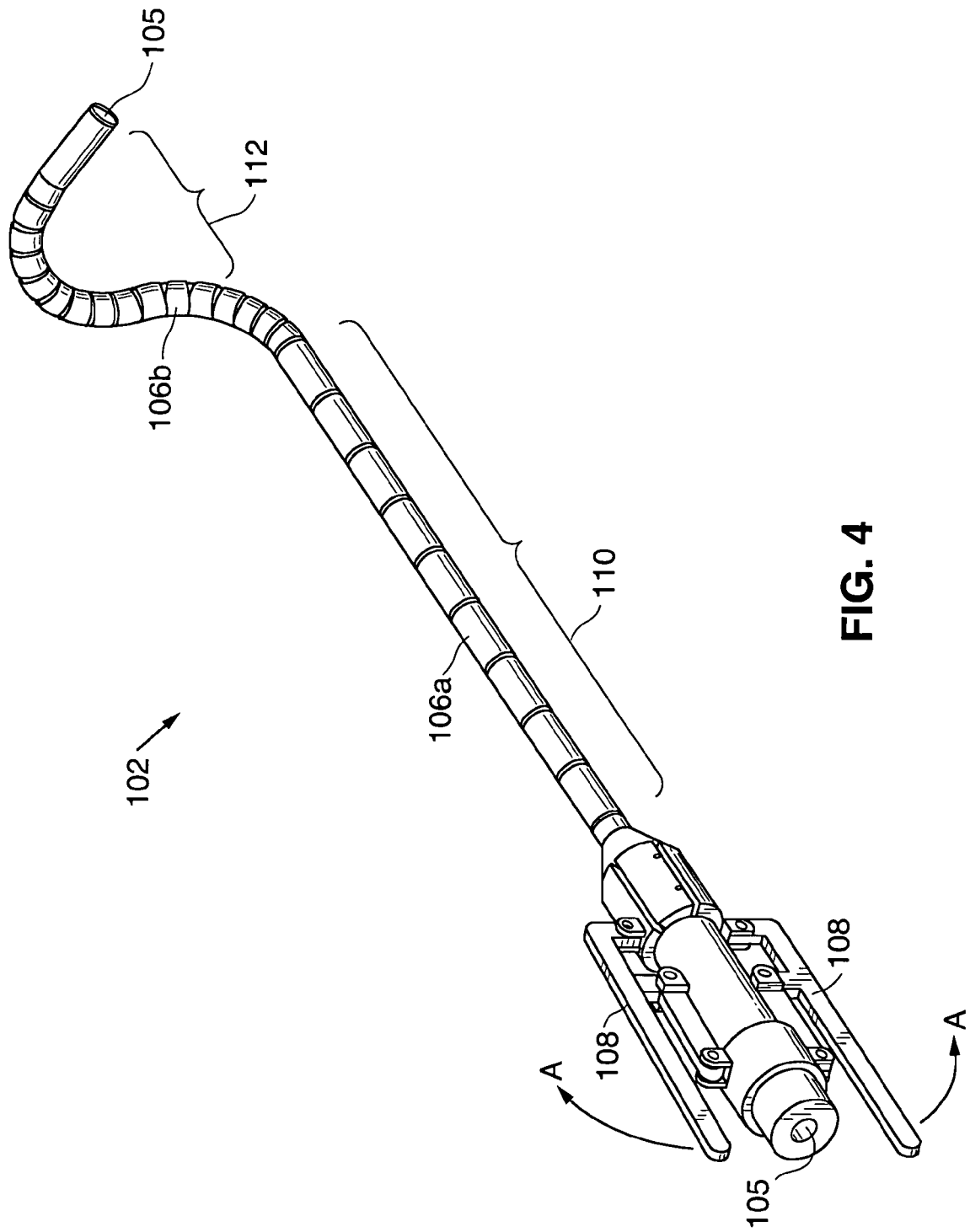
FIG. 4 is a perspective view of the spine of the system of FIG. 3.

A detailed view of the locking spine 102 is shown in FIG. 4. Referring to FIG. 4, locking spine 102 is formed of a plurality of spine segments 106a, 106b threaded over a pair of cables (not shown in FIG. 4) to form a flexible shaft. Each cable is coupled to a locking handle 108 that is moveable to the locked position shown in FIG. 4 to apply tension to the cables and to thereby rigidize the spine 102. To release the spine to a flexible state, the handles are moved in the direction of arrows A.

A plurality of the spine segments 106a are cylindrical segments having end faces that are perpendicular to the axis of the cylindrical segments. When a plurality of these cylindrical segments 106a is strung over the cables, they form a relatively straight spine section 110 when the handles 108 are locked. Others of the spine segments 106b have angular end faces and are assembled such that the chosen combination of angled segments 106b will give the distal portion 112 of the spine 102 a predetermined bend configuration when the spine 102 is locked as shown in FIG. 4.

Figure 5A:
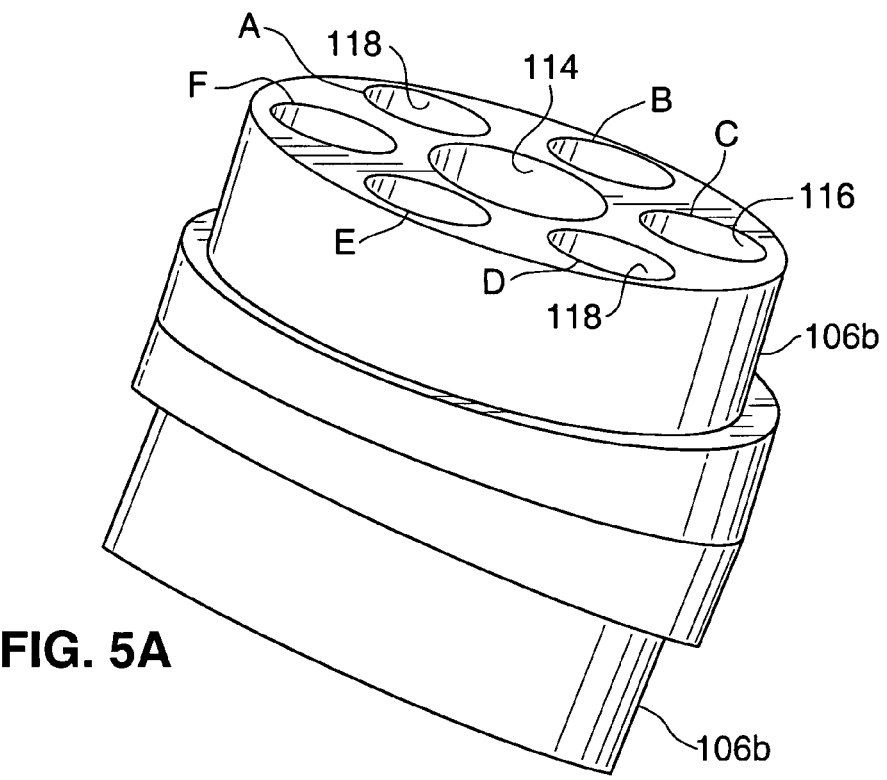
FIG. 5A is a perspective view illustrating two of the spine elements of the spine of FIG. 4.

FIG. 5A is a perspective view showing a pair of angled spine segments 106b assembled together. Each spine segment includes a central through hole 114 and a plurality of side through holes 116 surrounding the central through hole 114. Similar hole patterns may also be included in the cylindrical segments 106a that form the straight section of the spine. A variety of angled spine segments with end faces of different angles make up the curved distal portion of the spine. A group of spine segments with a predetermined combination of angles are selected to produce an overall shape for the spine that will support the associated tools in an optimal position for the procedure to be carried out within the body. In the FIG. 4 embodiment, spine segments are combined to create a multi-dimensional bend as shown.

The spine segments 106a, 106b etc. are "strung" onto cables 118 by passing each of the cables through one of the side through holes 116 in each of the spine segments. The side hole that is to receive the cable 118 for a particular spine segment 106b is selected based on the orientation in which the angled face of that segment must be placed to give the spine 102 the correct curve at that particular location on the spine 102. Thus, manufacturing instructions might list out a sequence of angled segments, giving for each segment the face angle that is to be used, as well as a designation of which side holes 116 are to receive each cable for that particular segment. An exemplary entry on the list might read "segment #10, angle 15°, cable #1 through hole A, cable #2 through hole D".

The central through holes 114 of the spine segments 106a, 106b align to form the lumen 105 (FIG. 4) of the spine 102.

Figure 5B:
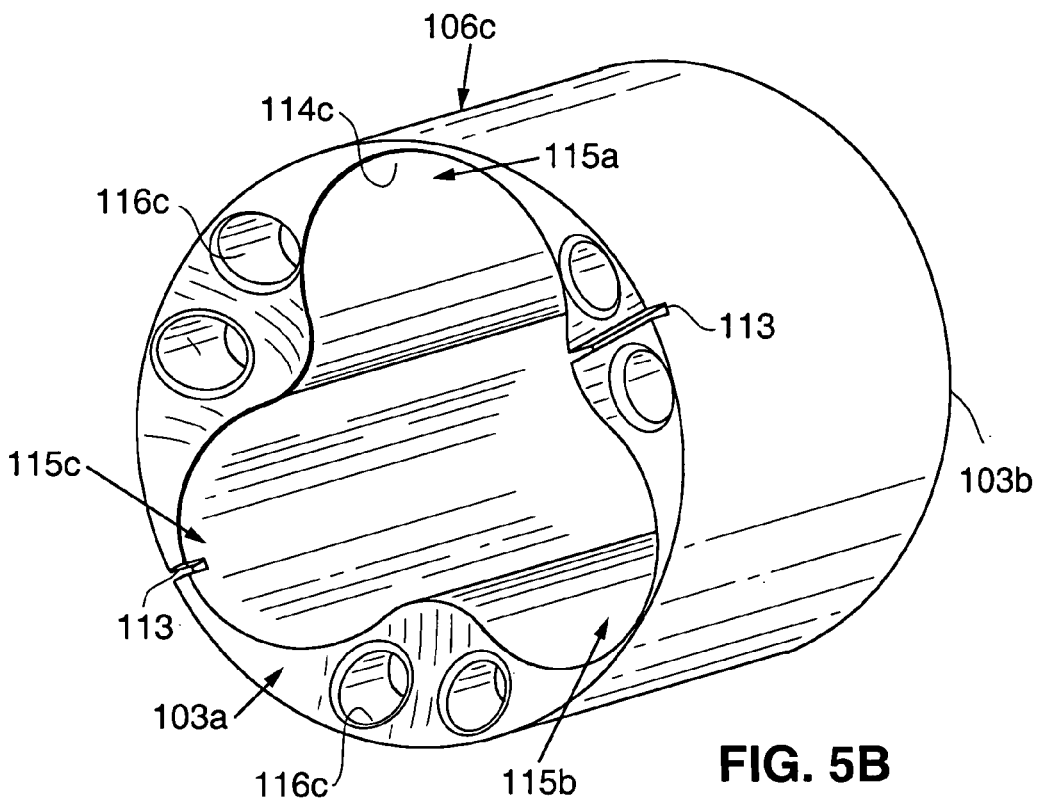
FIG. 5B is a perspective view of an alternative spine element for use in the system of FIG. 3.

FIG. 5B shows an alternative spine segment 106c having a concave end face 103a and a concave end face 103b, each of which comes together in a nesting relationship with adjacently placed spine segments. Slots 113 may be provided the concave face 103a for receiving corresponding mating ribs (not shown) on the convex face, allowing the segments to "key" together when assembled to minimize rotational movement of segments relative to one another.

In the FIG. 5B embodiment, the central through hole 114c includes a plurality of lobes 115a, 115b, 115c each sized and positioned such that one or more instruments passed through the through hole 114c can seat in a corresponding one of the lobes. This helps to maintain the instruments in a stable position within the elongate lumen of the spine formed by the assembly of the segments 106c. In this embodiment, the holes 116c through which the cables (not shown) are threaded are positioned in pairs as shown, although alternate patterns will be equally suitable.

Figure 6:
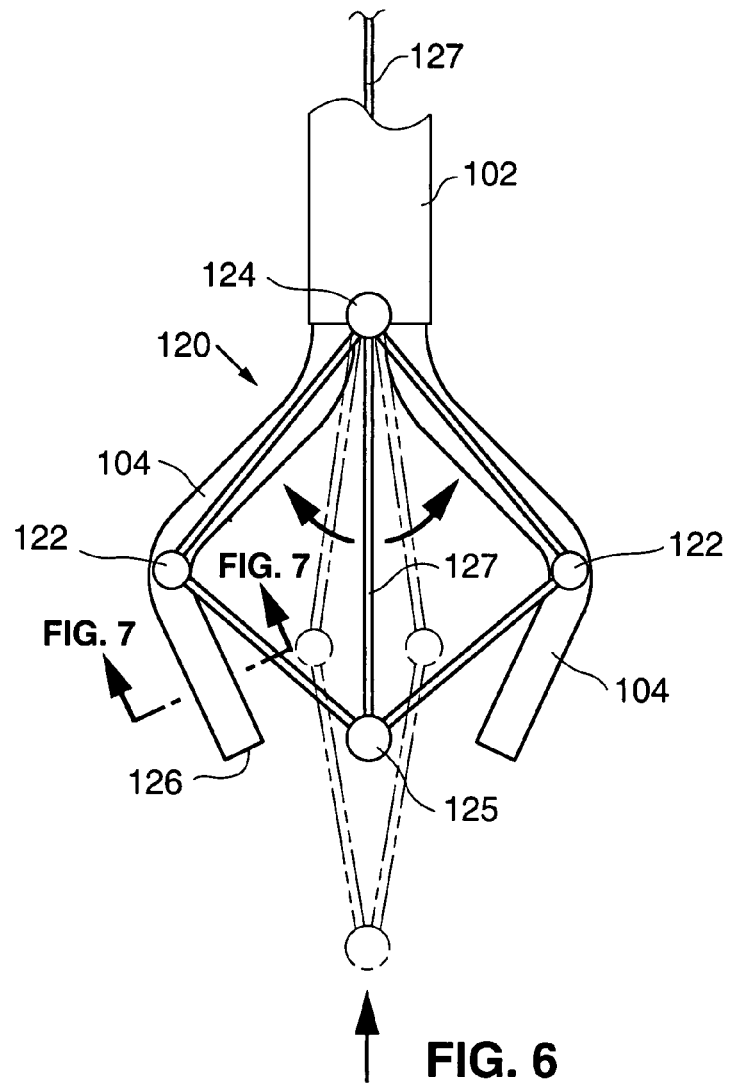
FIG. 6 is a perspective view showing the distal ends of the tool cannulas and linkage of the system of FIG. 3.

FIG. 6 is a perspective view of the distal end of the system 100 of FIG. 3, showing the distal ends of the tool cannulas 104. As with the first embodiment, the system 100 includes features that work in combination with the spine 102 to support and orient the tool cannulas 104 as appropriate for a given procedure. A linkage 120 is pivotally connected to the cannulas 104 at pivot points 122 and couples the cannulas 104 to the supporting spine 102. Linkage 120 also provides structural support for the distal portions of the tool cannulas 104 and maintains the relative orientation of the cannulas 104. As with the first embodiment and as shown in FIG. 3, the linkage 120 is attached to a pivot mount 124 on the distal portion of the locking spine 102. Another of the pivot mounts 125 is coupled to a pull wire 127 that extends proximally through spine 102 to a location outside the body. In an alternative embodiment shown in FIGS. 8A and 8B, pivot mount 125 may be coupled to the distal portion of a third longitudinal tool cannula 104a extending longitudinally from the spine 102, or to a similarly positioned tool shaft. As another alternative, either or both of the pivot mounts 124, 125 may extend into free space as shown in FIGS. 9 and 10 instead of being attached to the cannula 104a and/or spine 102.

The linkage 120 is positionable in a collapsed streamlined position in which tool cannulas 104 are near the longitudinal axis of the spine 102 for passage through the access cannula 10. Dashed lines in FIG. 6 show the arrangement of the linkage 120 and pivot mounts 122 when in the collapsed position. When in the streamlined position, the pivot mounts 122 are positioned side by side, thus orienting the tool cannulas 104 adjacent to one another. When in the deployed position, the pivot mounts are positioned approximately 3-7 inches apart, and more preferably approximately 4-6 inches apart.

Opening the linkage positions the cannulas 104 as shown in FIGS. 3, 6 and 8A-10 and thus points the instruments 32 positioned in the cannulas 104 generally towards an operative site. The linkage 120 of FIG. 6 may be deployed to the open position by withdrawing pullwire 127, whereas the FIGS. 8A, 8B embodiment can be deployed by advancing the distal end of the longitudinal tool cannula 104a in a distal direction to move the linkage 102 out of the access cannula and/or to deploy the linkage to the expanded position. In other embodiments, one or more of the pivot points 122, 124, 125 may be spring loaded to facilitate expansion of the linkage 120. Any combination of these deployment mechanisms, or others not specifically mentioned, may instead be used to deploy the linkage 120 in the peritoneal cavity.

Figure 11A:
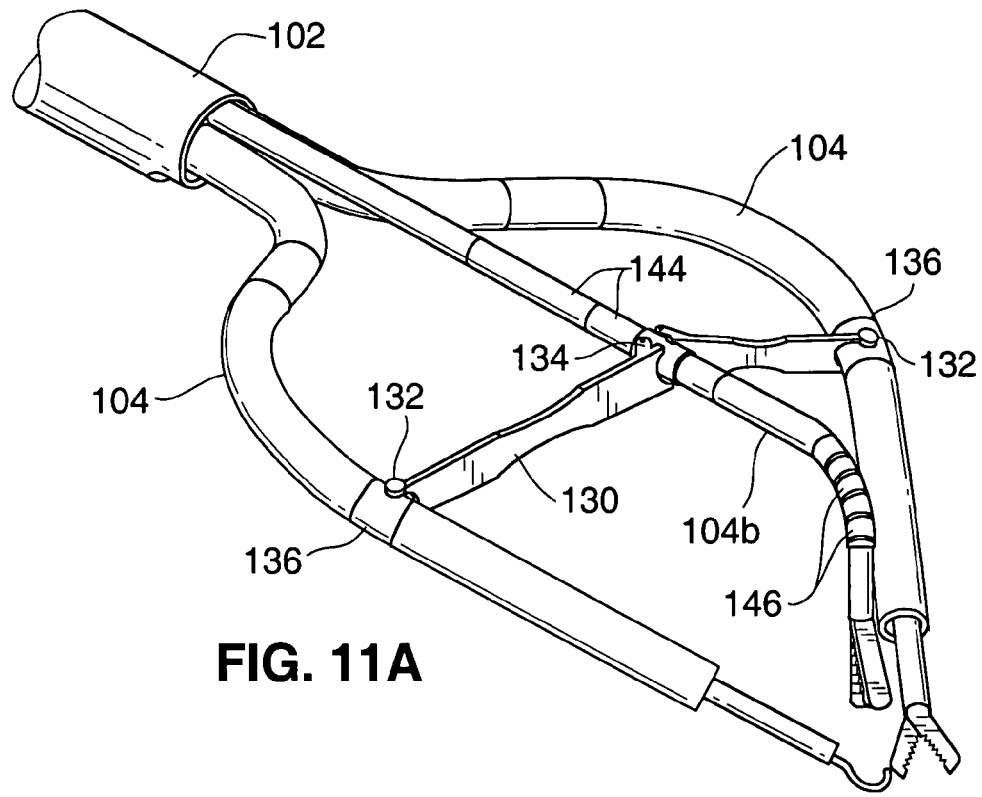
FIG. 11A is a top perspective view showing an alternative linkage assembly in combination with a spine, procedural cannulas, and a central retractor.
Figure 11B:
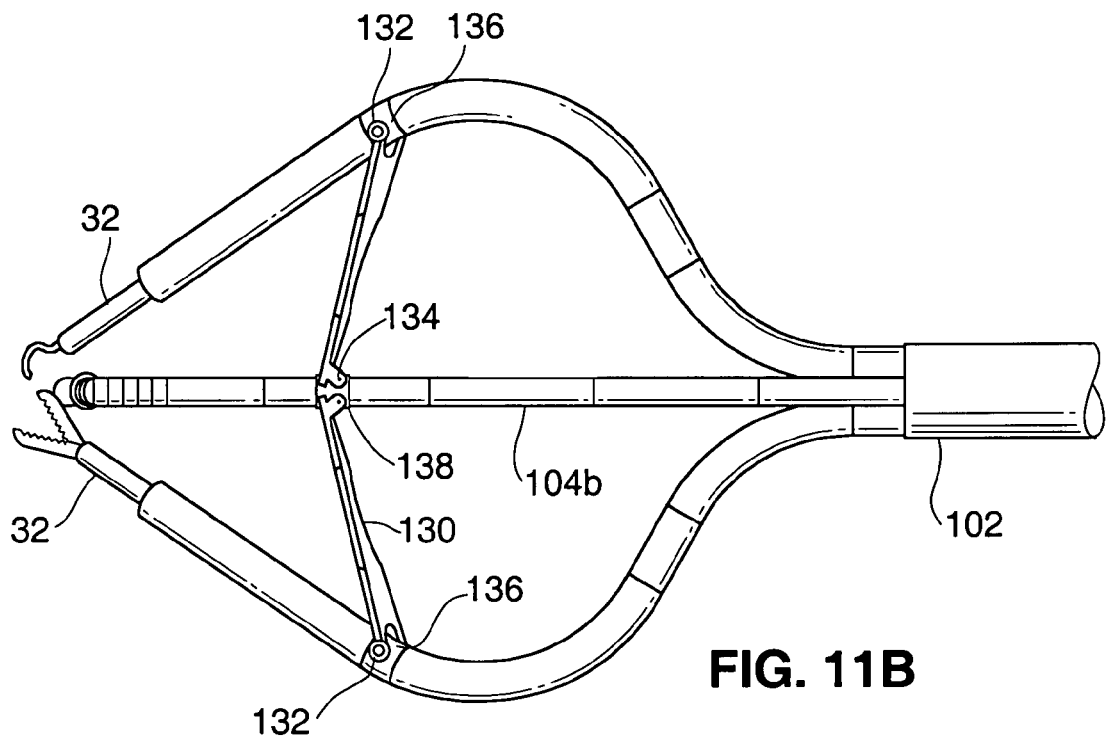
FIGS. 11B and 11C are a top plan view and a side elevation view of the linkage assembly of FIG. 11A.
Figure 11C:
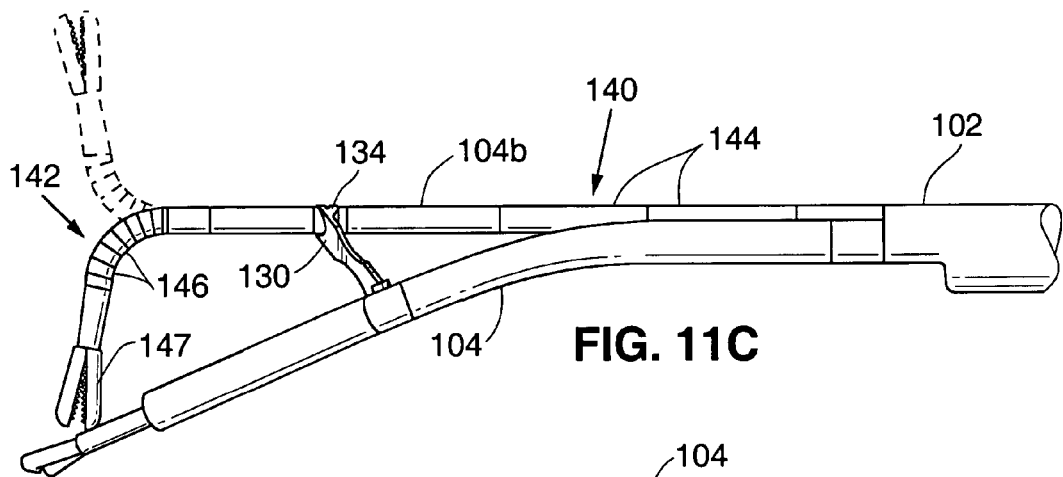
Figure 11D:
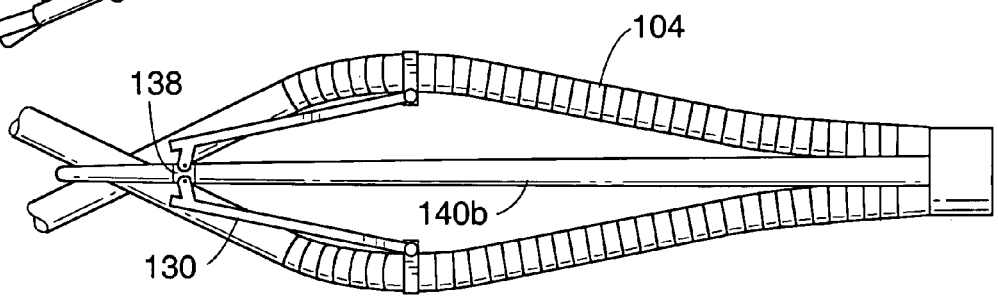
FIG. 11D is a top plan view of the linkage assembly of FIG. 11A in the streamlined position.

In another alternative shown in FIGS. 11A-11C, linkage 120a includes a pair of members 130. Each member 130 is attached by a corresponding one of the tool cannulas 104 by a first hinge 132 and to a central retractor 104b (or, alternatively, to a longitudinal tool cannula like cannula 104a of FIG. 8A) by a second hinge 134. Hinges 132 may be mounted to corresponding collars 136 on the tool cannulas 104, and hinge 134 may be on a similar collar 138 (FIG. 11B) on retractor 104b. When linkage 120a is in the collapsed position, members 130 extend in a distal direction as shown in FIG. 11D. To deploy the linkage 120a, central retractor 104b is withdrawn proximally, causing the members 130 to pivot at hinges 132, 134.

Referring to FIG. 11C, central retractor 104b includes a proximal section 140 and a distal section 142. Proximal section 140 is formed of a number of segments 144 strung onto one or more cables, with shorter segments 146 and an instrument tip 147 on the distal section 142. Cables within the retractor 104b are arranged such that the retractor becomes rigid when the cables are tensioned, and such that distal section 142 will deflect when the balance of tension within the cables is altered using controls outside the body. For example, retractor 104b may be deflectable towards and away from the body tissue as shown in FIG. 11C to allow tissue to be lifted by the retractor so the tissue may be acted upon by an instrument carried by one of the tool cannulas 104. Additional pull cables (not shown) are operable to open and close the jaws of the retractor tip 147.

In the disclosed embodiments, each tool cannula 104 preferably has a pre-shaped curve in its distal region. The curve orients the cannula 104 such that when the linkage is opened, instruments 32 (FIGS. 10A, 10B) passed through the central lumens 126 of the cannulas 104 can access a common treatment site. The preformed shape may be set using any of a number of methods. For example, the shaped region may have a segmented construction similar to the segmented spine 102, with the individual segments shaped to give the tool cannulas a shape that will orient the cannulas as shown in FIGS. 3, 9 and 10 when the cables running through the segments are tensioned. With this design, the entire length of the cannula may be segmented, or the distal portion may be formed of polymer tubing to allow flexibility. Alternatively, cannulas 104 can be made of pre-curved tubing having rigidity sufficient to prevent buckling during use. Reinforcing braid made of stainless steel or other materials may be formed into the walls of the tubing in the rigid section of the cannulas 104.

As with the FIG. 2A-2B embodiment, the distal end of each tool cannula 104 further includes a region that is deflectable in multiple directions to allow positioning and manipulation of the operative ends of the instruments. This avoids the need for sophisticated steerable surgical instruments. Instead, instruments 32 (FIG. 10) having flexible shafts are positioned in the tool cannulas 104, and steering of the instruments is achieved by deflecting the tool cannulas 104. Because the tools 32 are flexible, it may be necessary to "stiffen" the shaft of the tool 32 to allow the tool to be successfully used. A slideable stiffening cannula 33 (FIG. 10) may be advanced from within the tool cannula 104 over a portion of the shaft of the tool 32 to effectively stiffen the tool's shaft during the procedure, thus allowing the tool to be pressed into contact with body tissue without buckling. Other internal structures such as stiffening mandrels, reinforcing collars or braids, may instead be used for this purpose.

Figure 7:
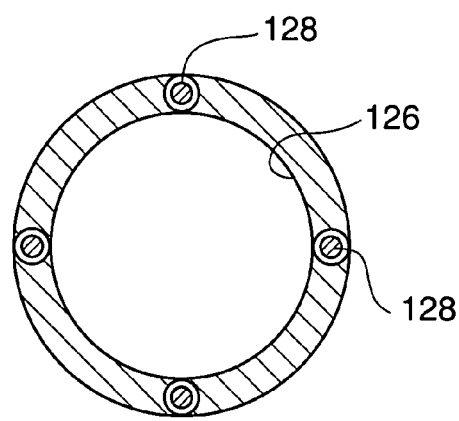
FIG. 7 is a cross-section view taken along the plane designated 7-7 in FIG. 6.
Figure 11E:
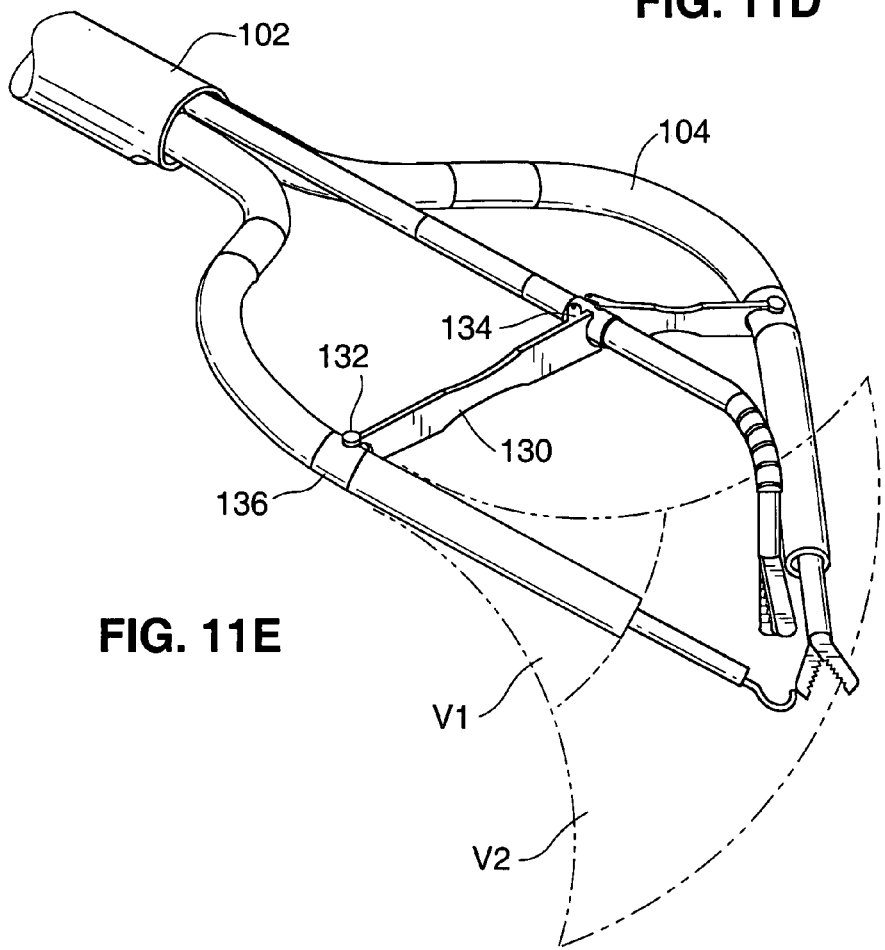
FIG. 11E is a perspective view similar to FIG. 11E illustrating exemplary movement patterns for the tool cannulas and associated tools.

In a preferred embodiment, deflection of the tool cannulas 104 is performed using a pullwire system. Referring to FIG. 7, pullwires 128 extend through corresponding pullwire lumens 130, preferably spaced at intervals of 90°. The distal ends of the pullwires are anchored in the distal sections of the cannula 104 such that the distal section of the cannula can be made to deflect in a desired direction by pulling on the desired combination of pullwires. FIG. 11E illustrates in dashed lines V1 a conical volumes defined by an exemplary movement pattern for the tool cannula 104, and the corresponding volume V2 defined by the tool 32 within the cannula 104.

Actuation of the pullwires is achieved using features that during use are positioned outside the body. A deflection system is provided that allows the user to intuitively actuate the pullwires for a particular one of the tool cannulas 104 by manipulating the handle 152 of the instrument 32 that resides within that tool cannula. For example, if the user wishes to have the distal end of a tool move in a downward direction, s/he will intuitively raise the handle 152 of that tool to cause the corresponding tool cannula to deflect downwardly, thus moving the tool to the desired position.

Referring to FIG. 3, the proximal ends of the pullwires 128 extend from the proximal ends of the cannulas 104 and feed into a corresponding deflection system, which in the illustrated embodiments is a control gimbal 148.

Figure 12A:
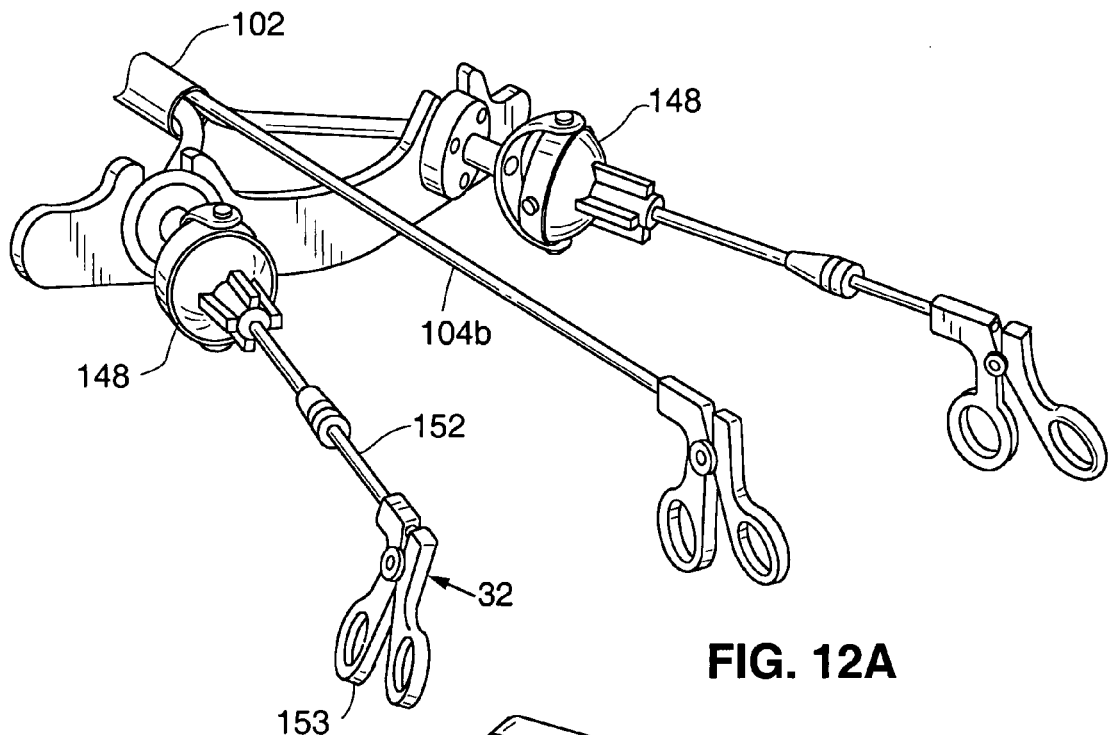
FIG. 12A is a perspective view of one embodiment of a user interface for the system of FIG. 3.
Figure 12B:
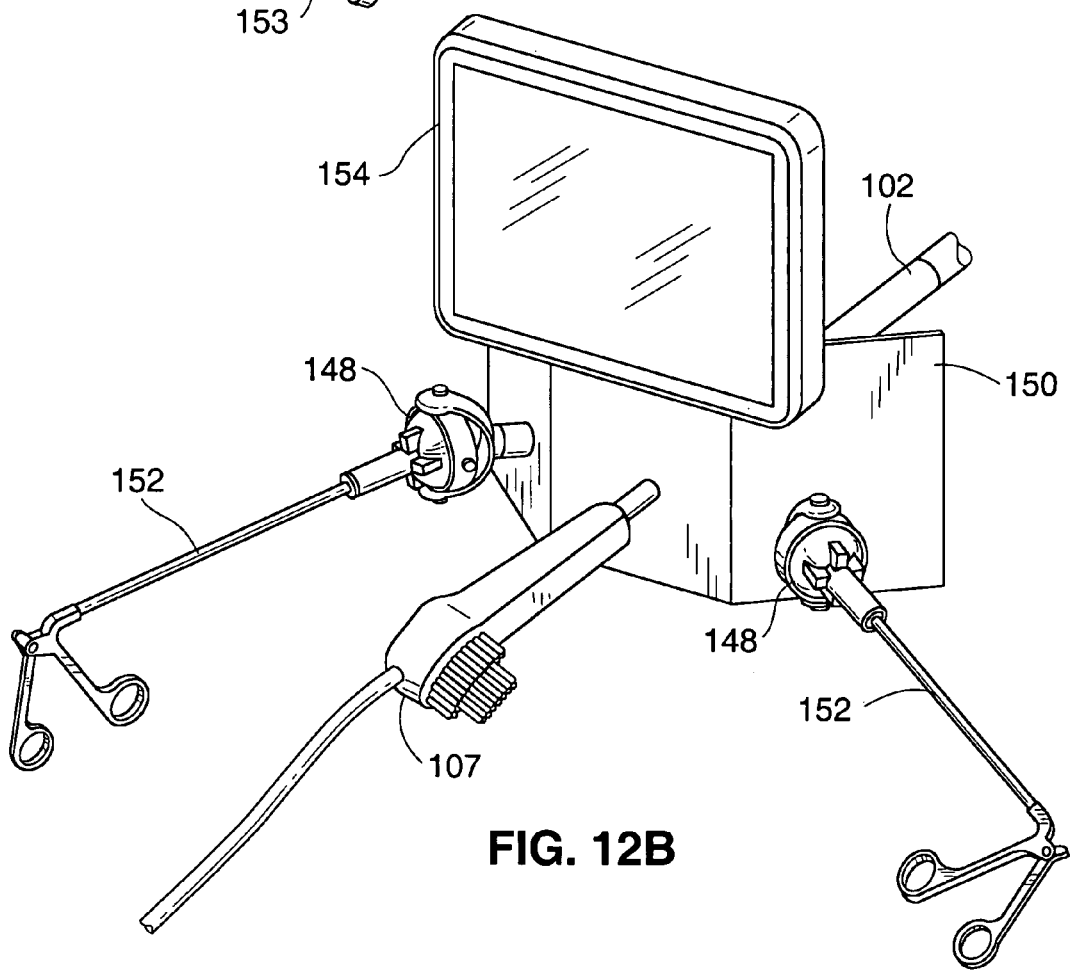
FIG. 12B is a perspective view of an alternative user interface for the system of FIG. 3.

The gimbal 148 may be mounted to a work stand 150 as shown in FIG. 12A. In use the work stand 150 may be set on top of the patient's torso or mounted to supports coupled to one or both side-rails of the surgical table, or carried on a cart. In either case, the work stand 150 is positioned to give the surgeon convenient and intuitive access to the handles 152 while s/he observes the procedure on an endoscopic display (not shown). As shown in FIG. 12B, use of the system may be facilitated by providing a "cockpit" for the user, coupling an endoscopic display 154 to the work stand 150 that supports the control gimbals 148, as well as the proximal controls for the endoscope 107, and other ports 111 for passing instruments through the access cannula to the peritoneal space.

The work stand 150 is proportioned to allow the surgeon to position his or herself in a comfortable position with his/her hands on the handles 153 of the tools 32. The work stand 150 preferably positions the tool handles 153 approximately 10-15 inches apart.

Figure 13:
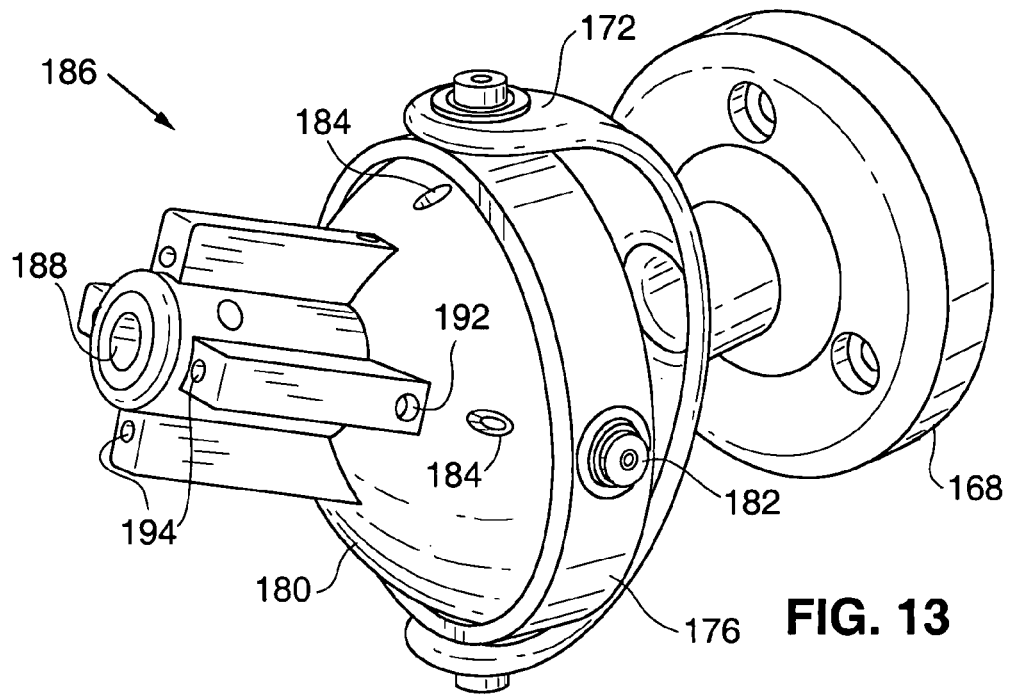
FIGS. 13 and 14 are a perspective view and a cross-sectional side view of a gimbal assembly.

A preferred control gimbal 148 is shown in FIG. 13. It includes a base 168 mounted to the work stand (not shown in FIG. 7) and having a tubular channel 170. A c-shaped mount 172 is connected to the base 168 and includes a through hole 174 continuous with the lumen of the tubular end piece 170. In a slight modification, the hole 174 might be accompanied by four separate through holes 174a-d might be used for receiving pull wires as in the FIG. 19 embodiment. A ring 176 is pivotally mounted to the mount 172 at pivot bearings 178. A semi-spherical ball 180 is pivotally mounted within the ring at pivots 182. Four pull-wire ports 184 extend from the interior of the ball 180 to its outer surface.

Instrument port 186 includes side channels 190 having distal openings 192 and proximal openings 194. The four pullwires 128 from the tool cannulas 104 extend through the tubular end piece 170 and each passes through hole 174, through the hollow interior of the ball 180, and out corresponding ones of the pull-wire ports 184 in the ball. The pullwires further extend into the instrument port side channels 190 and are secured there by anchors 196.

Figure 14:
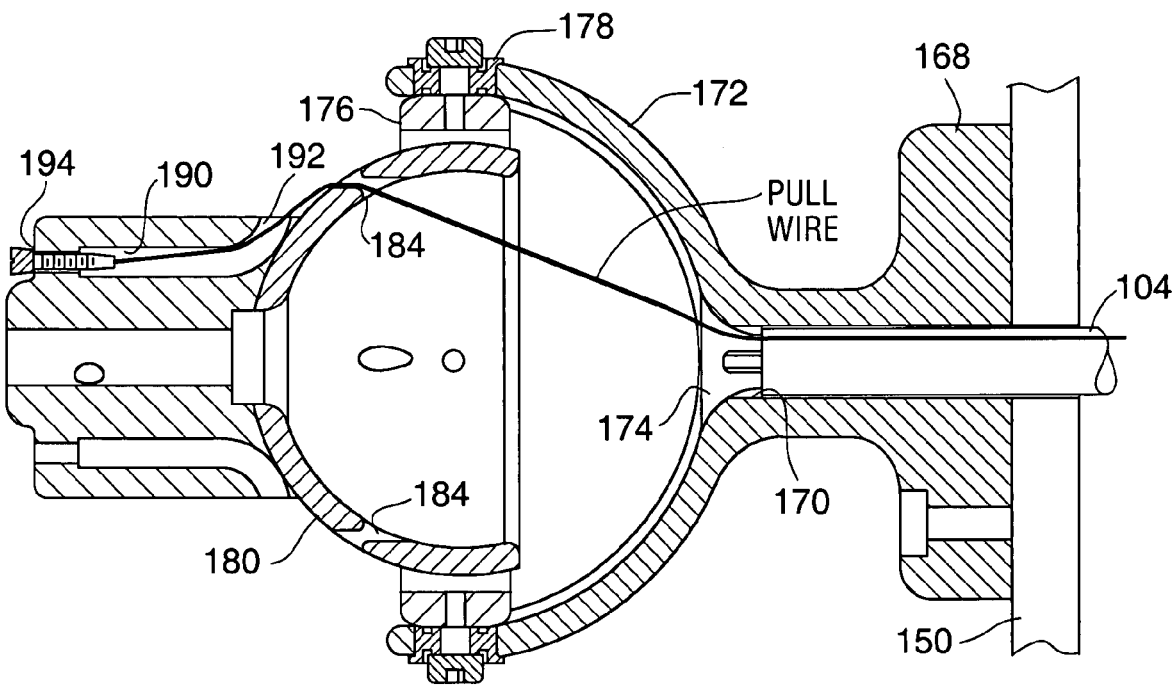

Instrument port 186 has a lumen 188 extending proximally from the spherical ball 180. The shaft 152 of an instrument 32 (see FIG. 12A, not shown in FIGS. 13-14) extends through the lumen 188 and the ball 180, through hole 174 in the c-shaped mount 172, and via tube 170 and the work stand 150 (FIG. 12A), into the corresponding tool cannula 104. The operative end of the instrument 32 extends from the distal end of the tool cannula 104.

When it becomes necessary for the surgeon to change the orientation of the distal end of an instrument 32, s/he need only intuitively move the handle 152 of that instrument and the distal portion of the instrument will deflect accordingly as a result of the action of the gimbal on the pullwires of the tool cannula. Vertical movement of the handle 152 will cause the ball 180 to rotate relative to pivots 182, thus applying tension to the upper or lower pullwire 128 to cause upward or downward deflection of the tool cannula 104 (and thus the distal end of the instrument 32). Lateral movement of the handle 152 will cause the ball 180 and ring 176 to rotate about pivots 178 and to therefore tension one of the side pullwires to change the lateral bend of the tool cannula 104. The control gimbal allows combinations of vertical and lateral deflection, giving 360° deflection as shown in FIG. 11E. Thus user may additionally advance/retract the tool 32 longitudinally within the tool cannula 104, and/or axially rotate the tool 32 relative to the tool cannula when required.

The control gimbal 148 includes a locking mechanism that allows an instrument orientation to be temporarily fixed until further deflection is needed. This feature allows a user to fix a trajectory for multiple instruments that are to be sequentially used at a particular location. For example, once the orientation of a tool cannula 104 is set, a certain step in the procedure may be performed using a first instrument passed through that cannula. When a subsequent step requiring a different instrument is to be performed, the instruments are exchanged without moving the tool cannula 104. This allows the second instrument to be advanced to the exact location at which it is needed without additional steering.

Figure 15A:
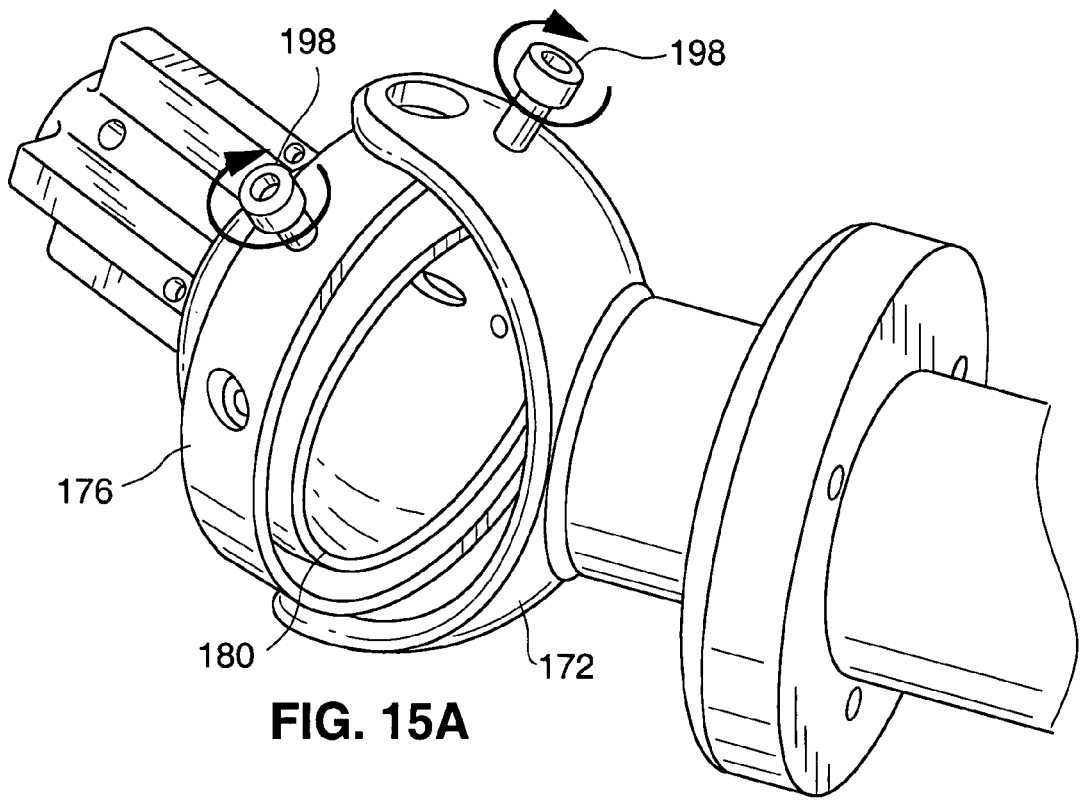
FIGS. 15A and 15B are perspective views of the gimbal assembly of FIG. 13 showing two exemplary locking mechanisms.
Figure 15B:
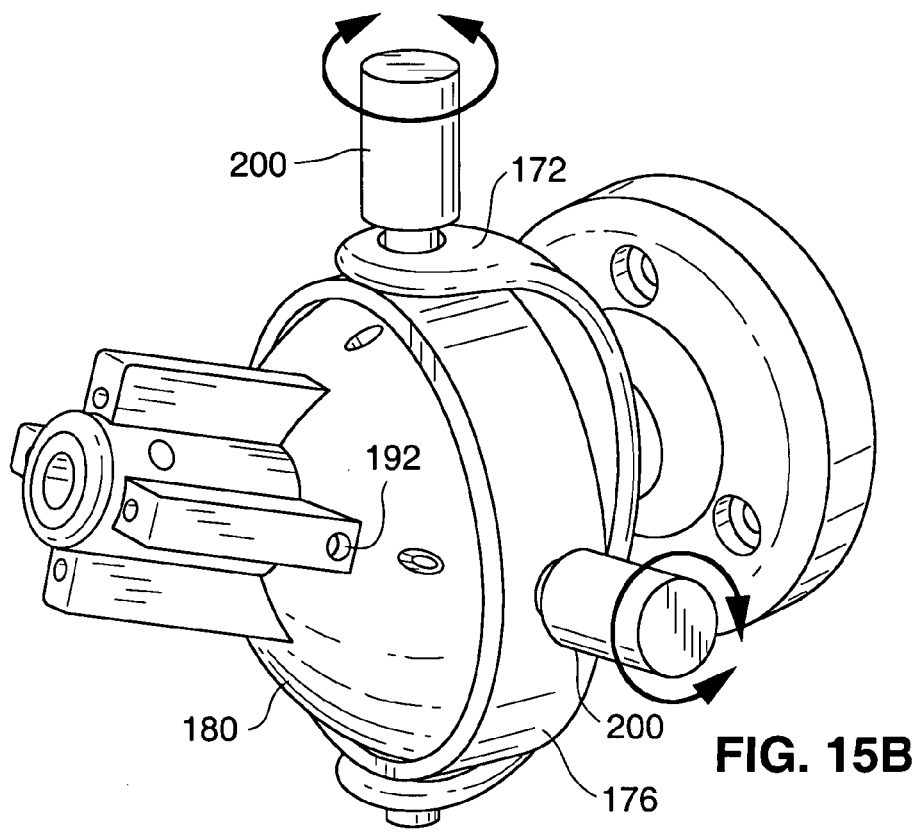

One exemplary locking mechanism includes a pair of locking screws 198 that are tightened as shown by arrows in FIG. 15A to lock the C-mount 172 to the ring 176 and to lock the ring 176 and the ball 180. Alternatively, as shown in FIG. 15B, a simple pneumatic shaft lock 200 could be employed on each of the gimbal's pivot axes. A solenoid or similar device might be used in place of the pneumatic lock 200.

Figure 16A:
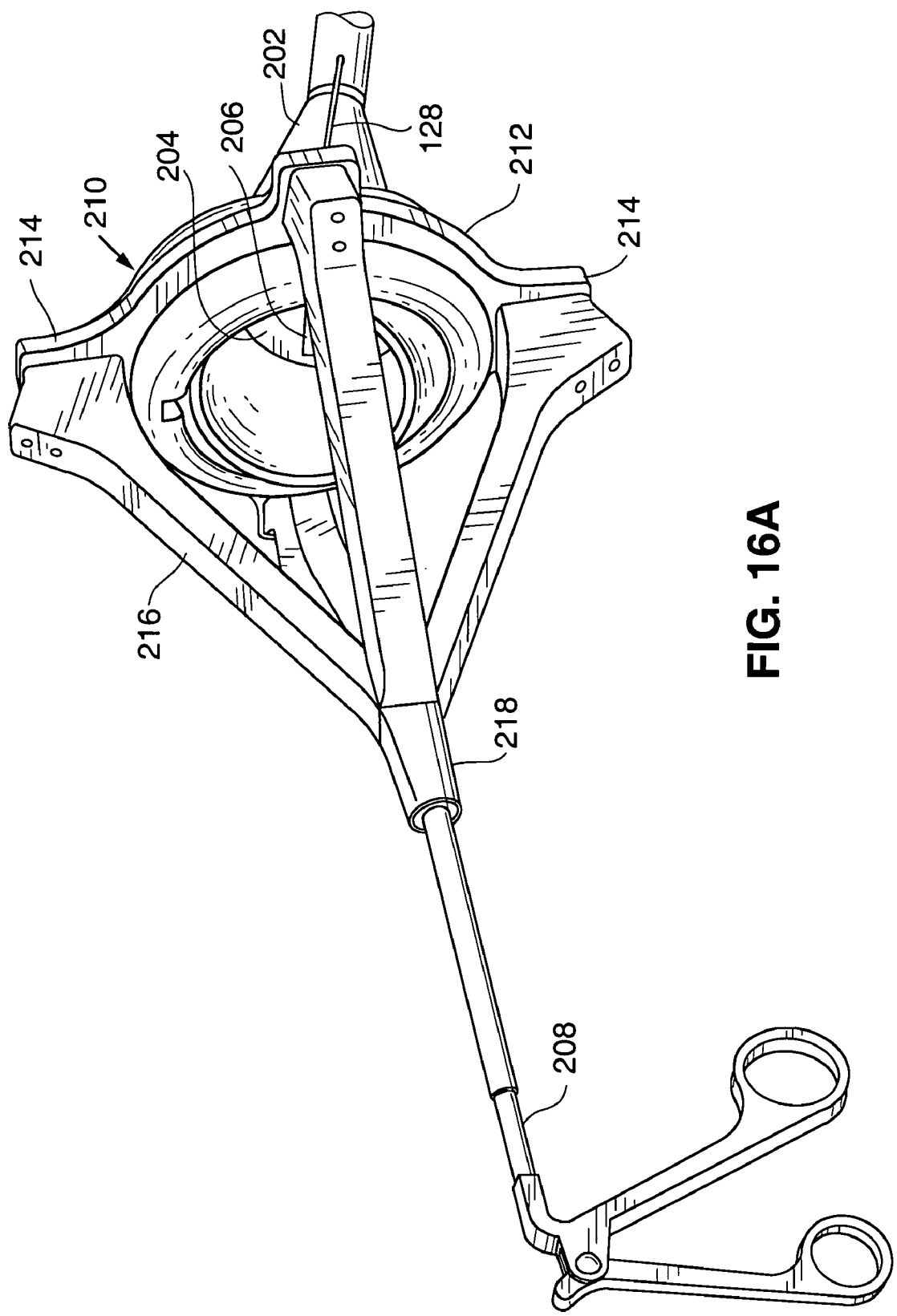
FIGS. 16A and 16B are perspective views of an alternative gimbal system.
Figure 16B:
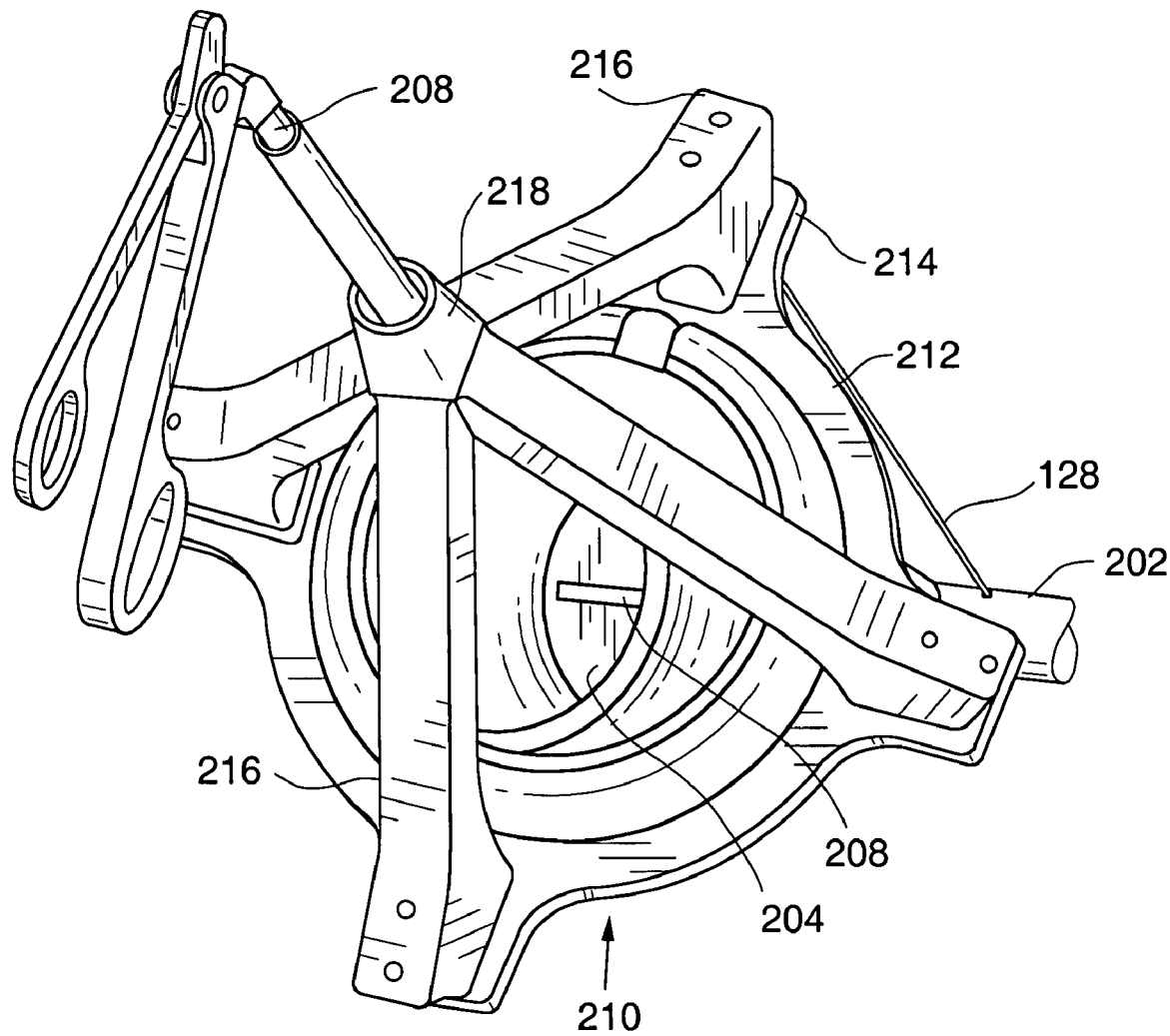

An alternate gimbal arrangement is shown in FIGS. 16A and 16B. As shown, a cone shaped instrument port 202 is mounted to the proximal end of each cannula, and includes a diaphragm seal 204 having a slit 206 sealable around an instrument shaft 208 passed into the instrument port 202. In FIGS. 16A and 16B only the handle of instrument shaft 208 is shown to permit easier viewing of the surrounding features.

A gimbal 210 includes a collar 212 mounted on the instrument port 202 and four wings 214 radiating from the collar 212. Each pullwire 128 is coupled to one of the wings 214. Struts 216 extend proximally from the wings 214 and are joined to a sleeve 218 through which a portion of the instrument shaft 208 extends. Collar 212 is moveable relative to the instrument port 202, and in particular collar 212 is rotatable about its central axis, and pivotable in multiple directions. Movement of the collar 212 places one or more of the pullwires 128 under tension and results in deflection of the cannula 104. Since the instrument shaft 208 is coupled to the collar 212 by struts 216, a user can manipulate the instrument shaft 208 handle in an intuitive manner similar to a joystick to allow the user to steer the distal end of the cannula 104 in the desired direction.

Figure 17:
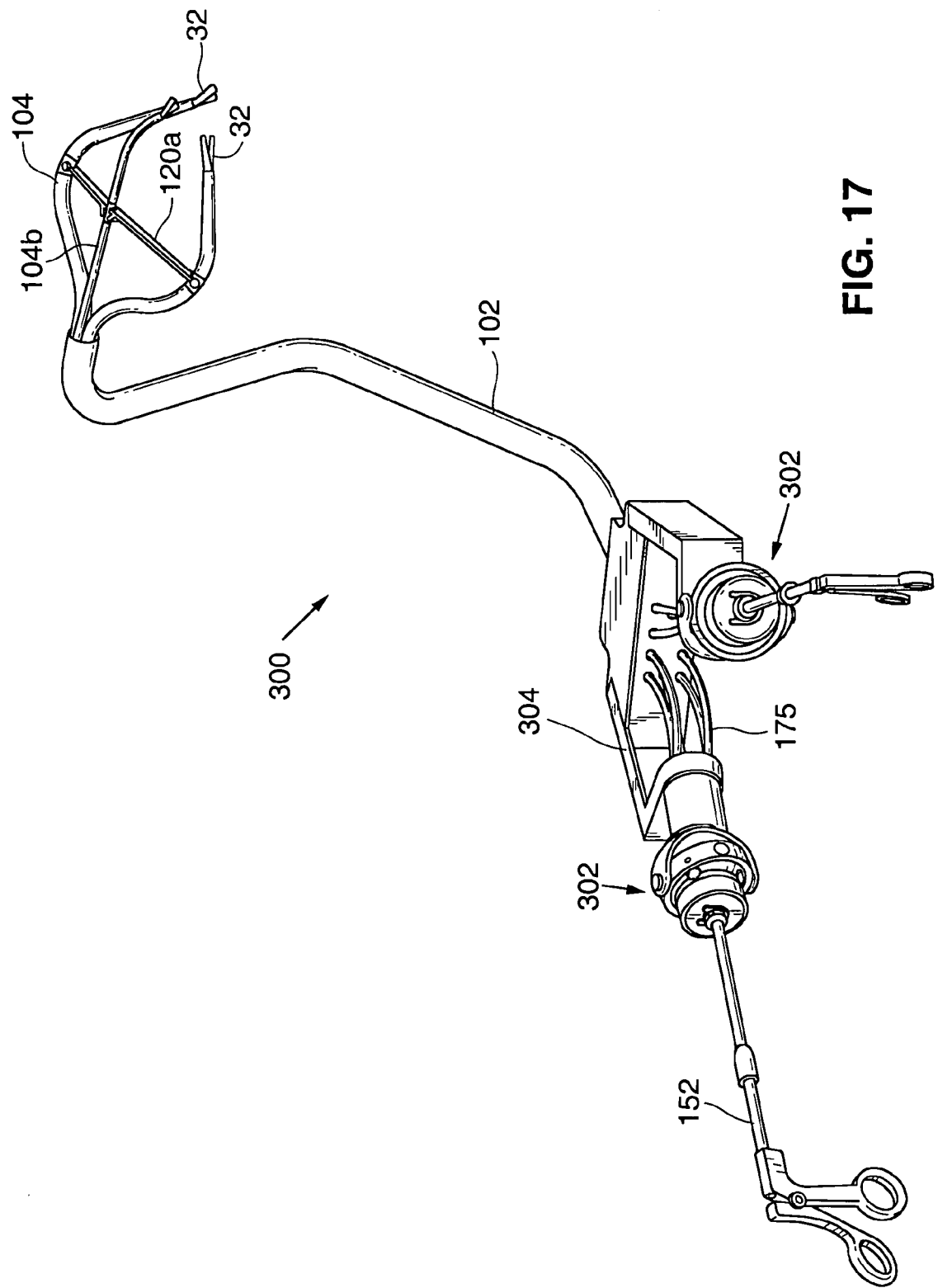
FIG. 17 is a perspective view of a third embodiment of a procedural cannula and support system.
Figure 18:
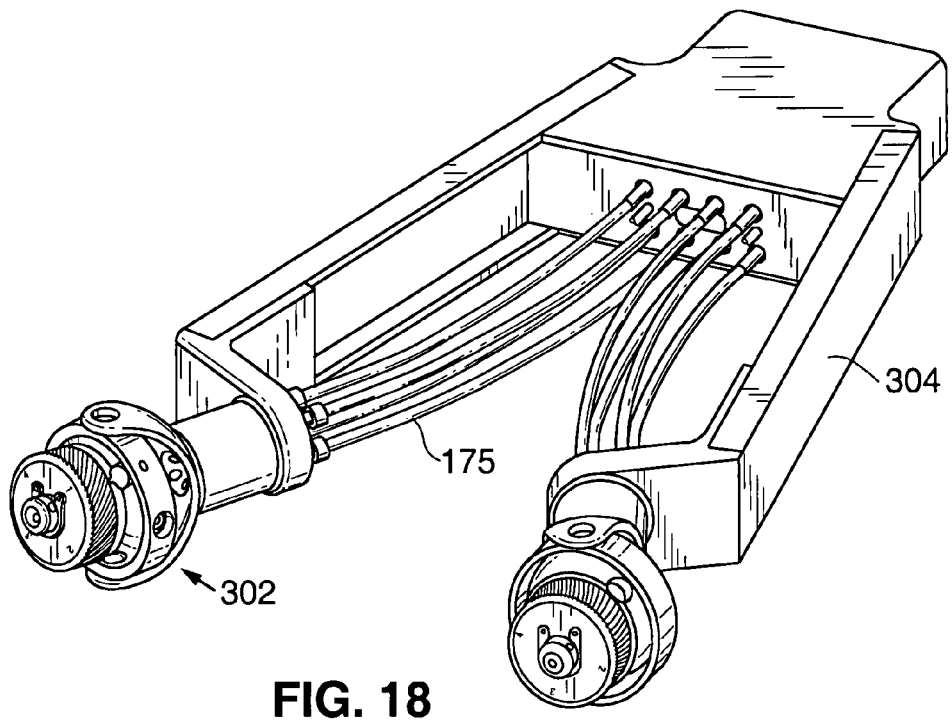
FIG. 18 is a detailed perspective view of the proximal end of the system of FIG. 17.

FIG. 17 illustrates an alternative natural orifice surgical system 300. System 300 includes features that are largely similar to those described elsewhere. For example, the system 300 uses the linkage 120a of FIG. 11A, and a gimbal system similar to that described in connection with FIG. 13. The system 300 differs from the earlier embodiments in that it allows a user to adjust the sensitivity of the gimbals. In other words, the gimbal can be fine tuned such that the amount of deflection of the tool cannulas corresponds directly to the amount by which the user moves the tool handles 152 within the gimbal system, or the amount of deflection can be greater than or less than the corresponding movement of the tool handles.

Figure 19:
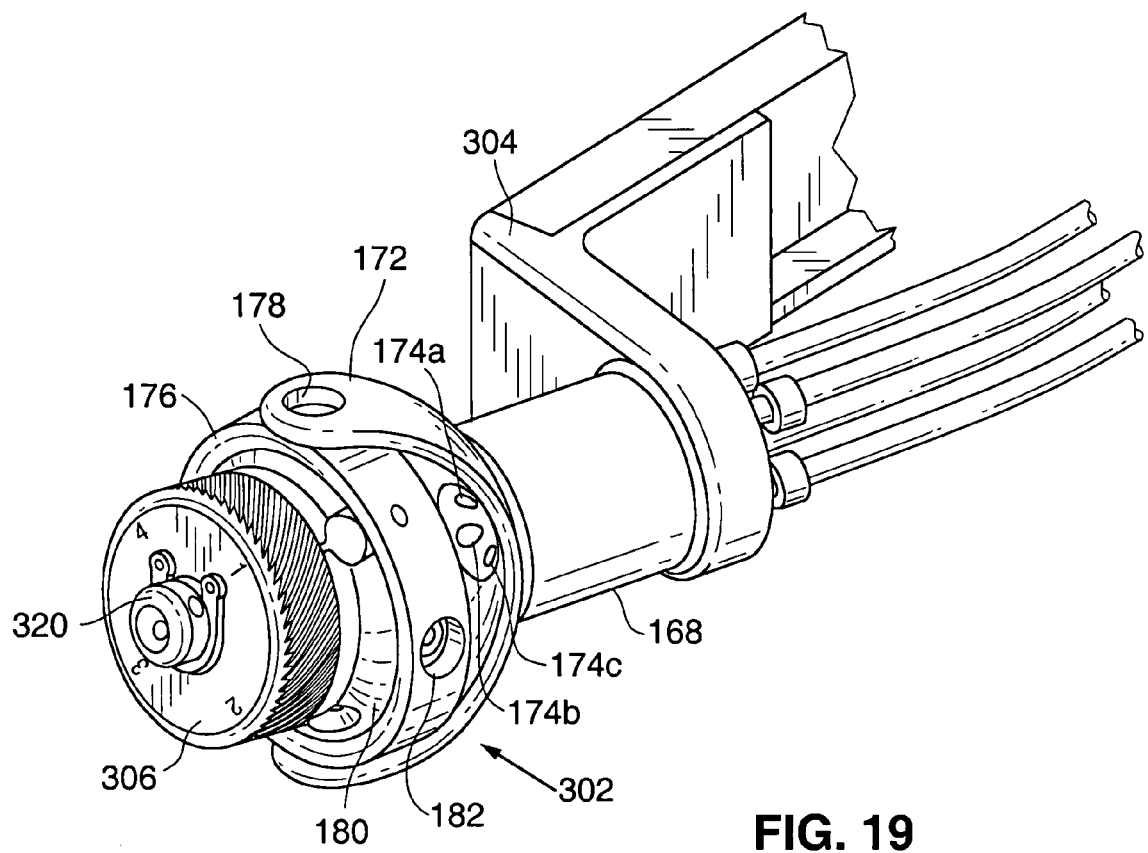
FIG. 19 shows the gimbal system of the FIG. 17 embodiment.

Referring to FIG. 19, many of the features of the gimbal 302 are similar to those of gimbal 148 of FIGS. 12 and 13. These similar features include base 168, which is coupled to frame 304. Four through-holes 174a-d (three of which are visible in FIG. 19), one for each pull wire, extend from c-shaped mount 172 through base 168. The pullwires feed into the through-holes 174a-d from cable housings 175 that pass through the frame 304. The more distal segments of the pullwires extend from the from the frame 304 into the tool cannulas 104 extending distally from the frame 304.

A ring 176 is pivotally mounted to mount 172 at pivots 178, and semi-spherical ball 180 is pivotally mounted within the ring 176 at pivots 182.

The gimbal 302 of FIG. 19 differs from the gimbal 148 of FIGS. 12-13 in its inclusion of a microadjustment assembly 306. As with the prior gimbal arrangements, the four pullwires of one of the tool cannulas terminate in the gimbal at 90 degree quadrants. Motion of the instrument shaft 152 (FIG. 17) alters the tension on the various pullwires, which causes deflection of the tool cannula tip and corresponding movement of the tool within the tool cannula. The effect lever arm of each pull wire is altered in the FIG. 19 embodiment by moving the point of termination of each pull wire towards or away from the gimbal's center of rotation. Moving the pullwire terminations away from the center of rotation causes movement of the tool cannula 104 to be amplified relative to the movement of the tool handle 152, whereas moving the pullwire terminations towards the center of rotation decreases the amplification.

Figure 20:
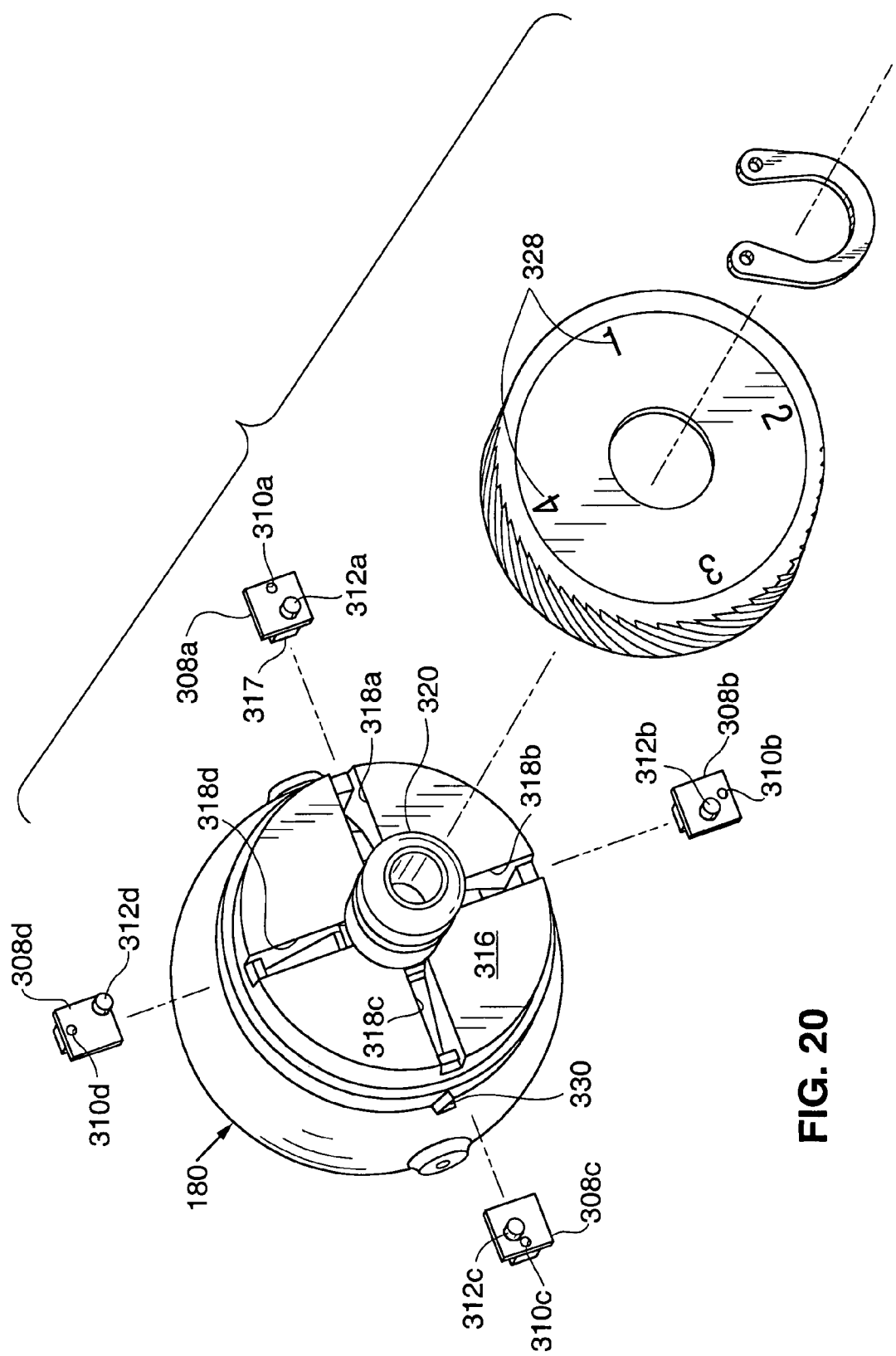
FIG. 20 is an exploded view of the gimbal system of FIG. 19.
Figure 21:
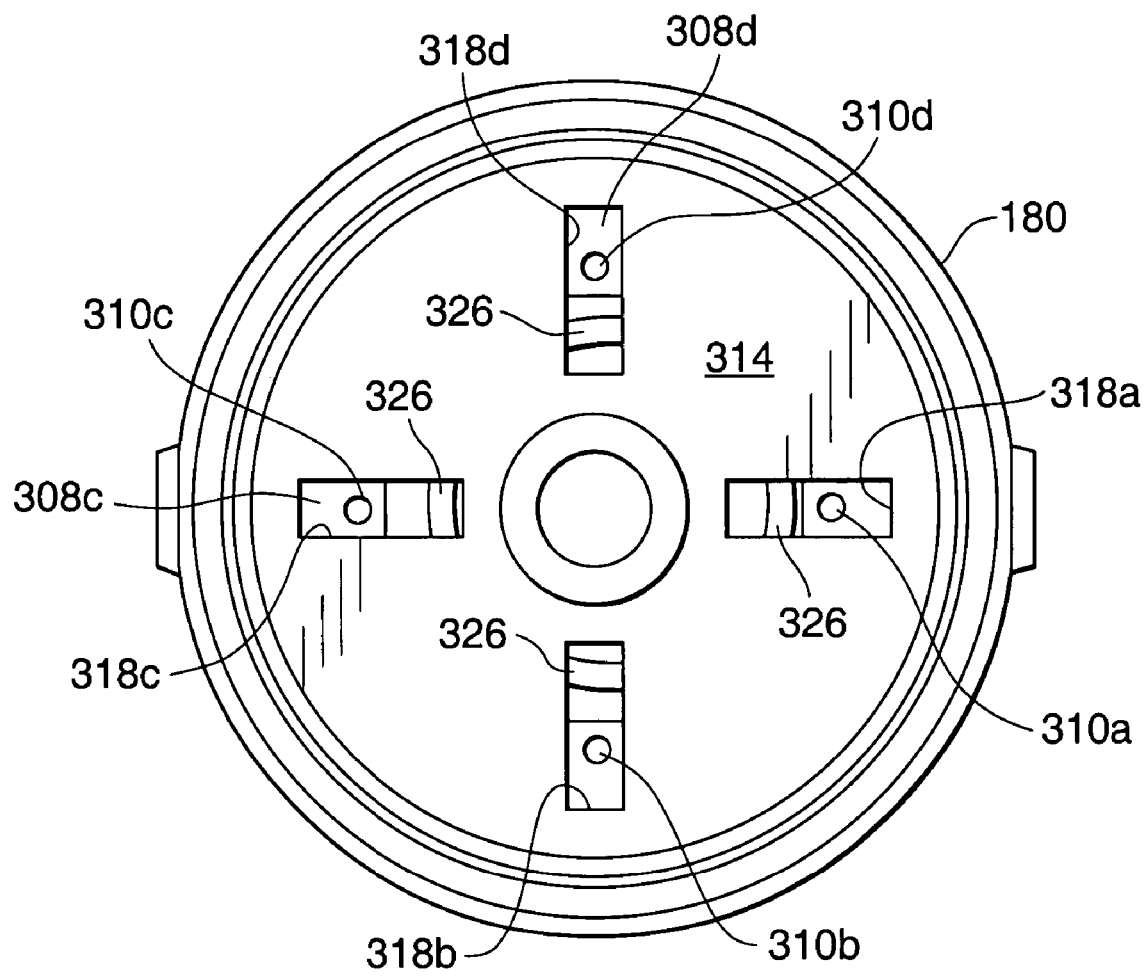
FIG. 21 is a plan view of the distal surface of the ball of the gimbal system of FIG. 19.

Ball 180 includes a distal surface 314 as shown in FIG. 21A, and a planar proximal surface 316 as shown in FIG. 20. Four radial slots 318a-d extend through between the surfaces 314, 316. Referring to FIG. 20, four sliding terminal plates 308a-d, each including a pullwire terminal 310a-d and a proximally-extending follower pin 312a-d, are positioned in contact with the planar proximal surface 316. A peg 317 on the distal side of each terminal plate is received in the corresponding one of the slots 318a-d.

Each pullwire used to deflect the tool cannula extends through one of the slots 318a-d and is anchored within a terminal 310a-d of one of the four sliding terminals 308a-d. FIG. 21A shows the distal facing side 314 of the ball 180, with the terminals 310a-d positioned over the slots 318a-d. The pull wires themselves are not shown.

Figure 22:
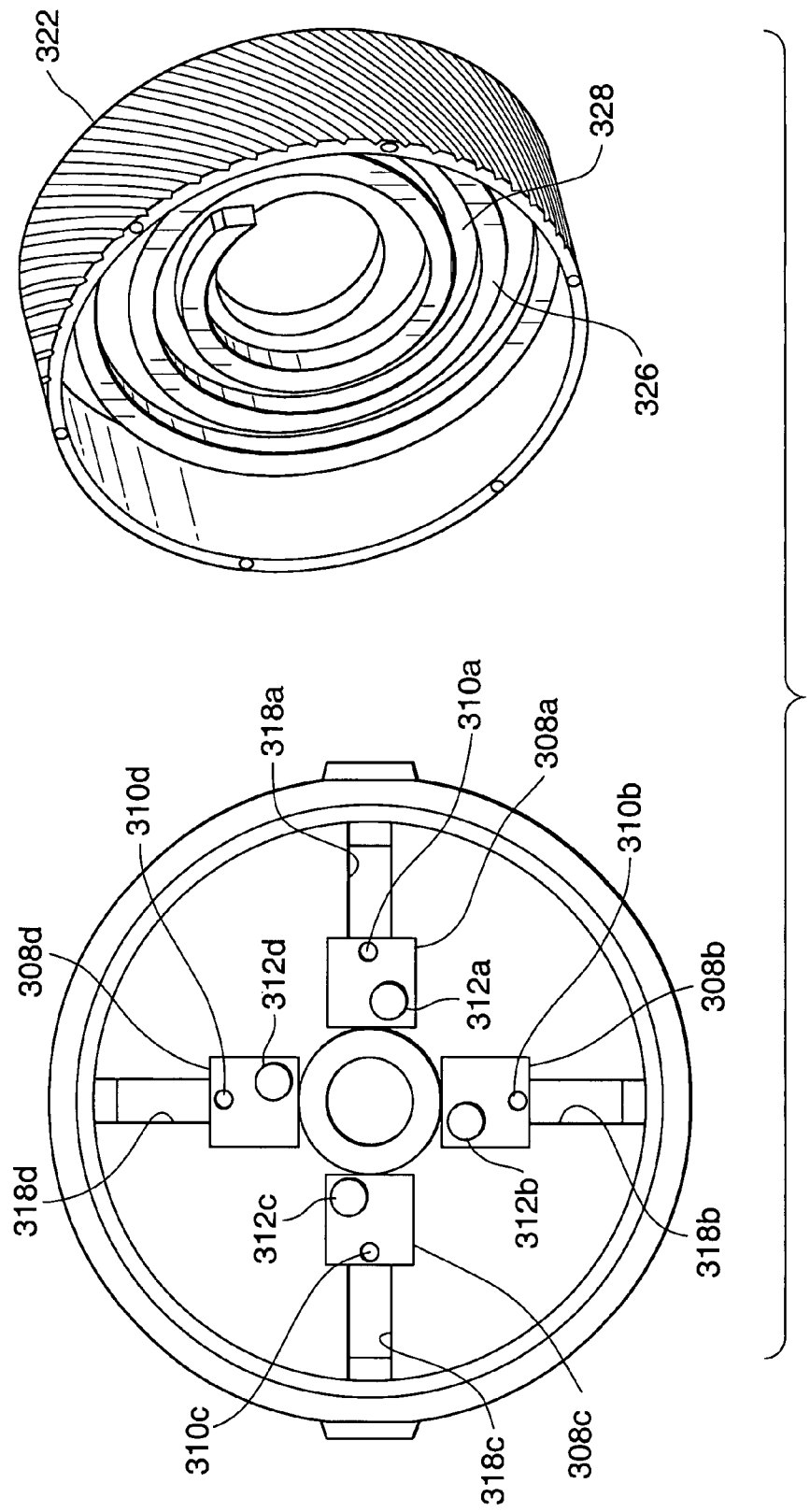
FIG. 22 is a plan view of the proximal surface of the ball of FIG. 21, with the cap removed and shown in perspective view.

A tubular instrument port 320 is centrally positioned on the proximal surface 316 of the ball 180. A retainer cap 322 covers the surface 316, such that the instrument port 320 extends through a central opening 324 in the retainer cap. The sliding terminal plates 308a-d are sandwiched between the surface 316 and the retainer cap 322. FIG. 22 shows the cap 322 removed from the ball 180. The inner, distal facing, surface of the cap 322 includes a spiral rib 326 defining a spiral shaped slot 328. Each of the follower pins 312a-d of the terminal plates 308a-d are disposed within the spiral slot 328.

A retaining ring 330 is engaged with the instrument port 320 and functions to hold the cap 322, terminal plates 308a-d, and ball 180 together such that the follower pins 312a-d remain within the spiral slot 328. Cap is rotatable in clockwise and counterclockwise directions relative to the instrument port 320. Rotation of the cap will increase or decrease the sensitivity of the gimbal system. More specifically, if the cap is rotated in a first direction, the spiral rib 326 will cause the pins 312a-d to advance through the spiral slot towards the outer circumference of the cap, causing the terminal plates to slide radially outwardly within slots, thereby increasing the sensitivity of the gimbal system. If the cap is rotated in a second direction, the pins will advance through the spiral slot toward the center of the cap, causing the terminal plates to slide radially inwardly within the slots so as to loosen the tension on the pullwires and to decrease the sensitivity of the gimbal system. Markings 328 on the cap 322 and a corresponding pointer 330 instruct the user as to the level of sensitivity achieved when the cap is in one of the designated rotational positions relative to the pointer 330.

In alternative configurations for adjusting gimbal sensitivity, the user may have the option to set different sensitivity levels for different ones of the pull wires.

The system is preferably packed in a kit containing instructions for use instructing the user to use the system in the manner disclosed herein.

Figure 23:
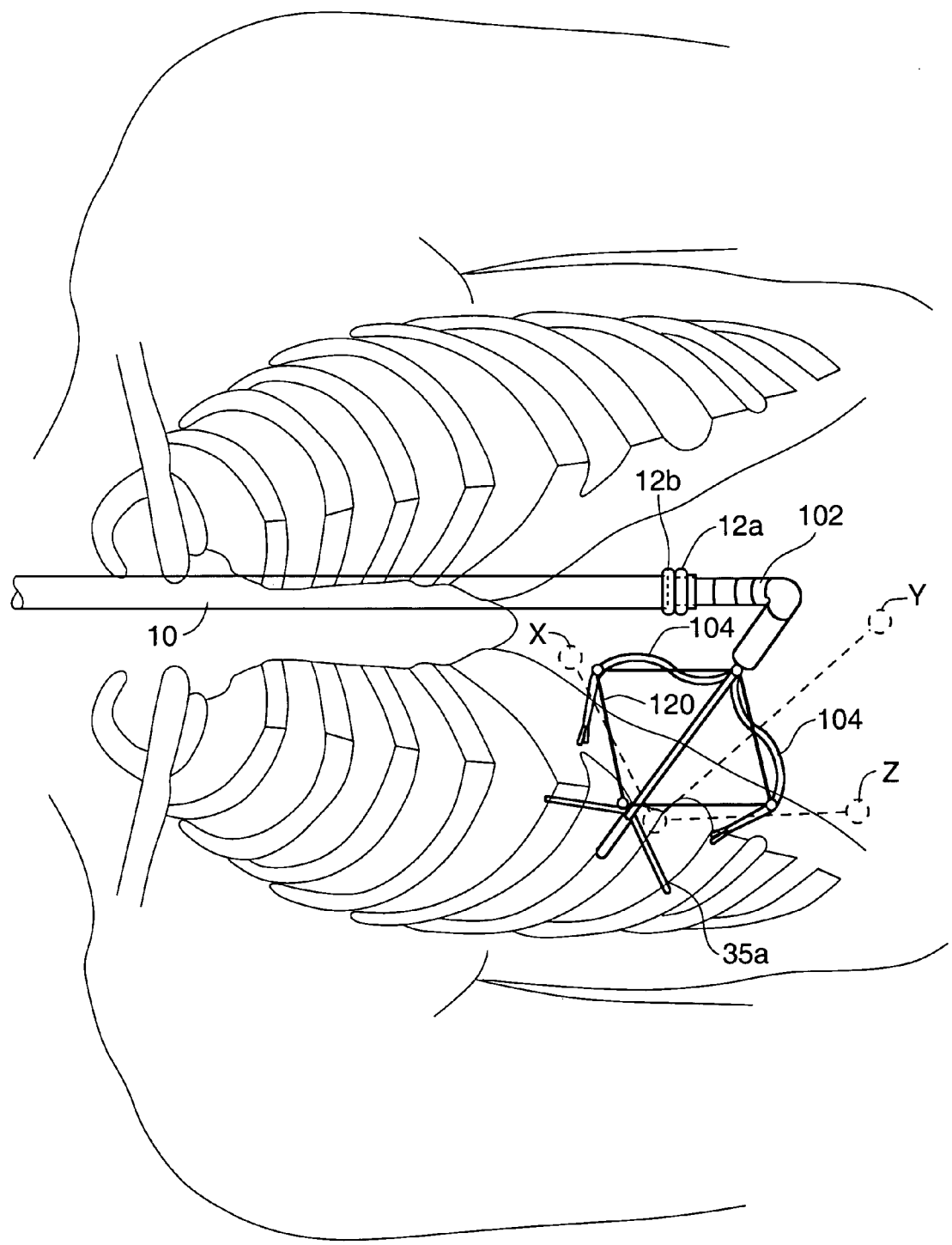
FIG. 23 is a top view similar to FIG. 2B showing the system of FIGS. 9 and 10 in use for surgery on a liver.

FIG. 23 schematically illustrates use of the system of FIGS. 9 and 10 as used such as for a cholecystectomy procedure. According to such a procedure, the access cannula 10 is placed transorally and moved into the peritoneal cavity via a left anterior stomach wall puncture. The access cannula 10 is anchored in a stomach incision as described above. The locking spine 102 is introduced into the peritoneal space and made rigid (via application of tension on the cables as described above) such that it is oriented towards the procedural site as shown. The liver retractor 35a is used to lift and retract the liver superiorly away from the gallbladder and the operational area of the instruments 32. Instruments 32 are advanced through the tool cannulas and used to perform the procedure. Tool cannulas 104 are deflected as needed to manipulate the instruments. Whereas prior art laparoscopic procedures involve formation of three surgical ports or incision X (tool port), Y (endoscope port), Z (tool port) to perform the cholecystectomy procedure, use of the disclosed system allows the procedure to be performed less invasively while allowing the surgeon to carry out the procedure from the same familiar perspective from which s/he would have performed the laparoscopic procedure.

Figure 24:
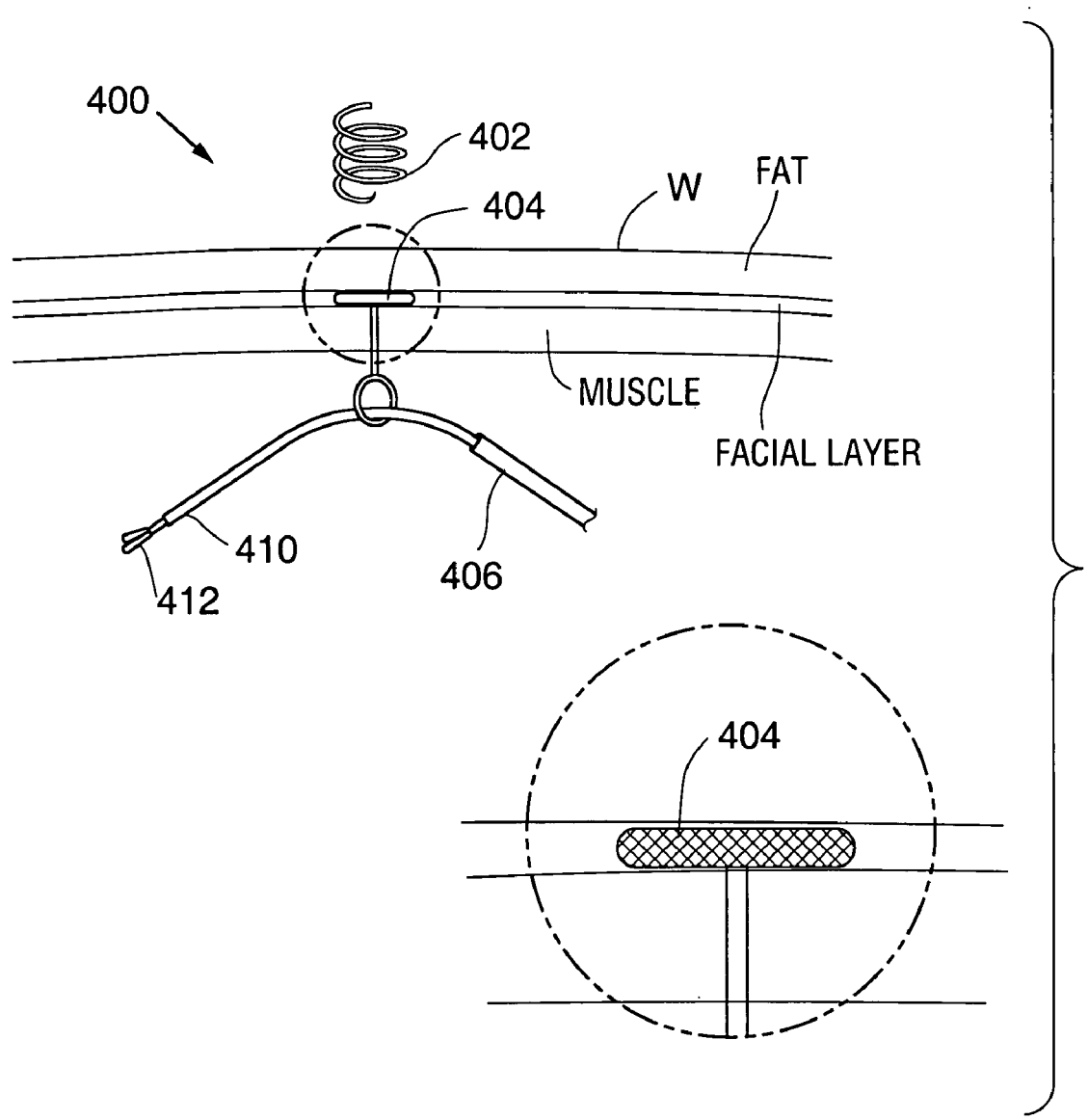
FIG. 24 schematically illustrates an abdominal cavity and shows an alternative support system mounted to the interior wall of the abdominal cavity.

The embodiments disclosed above utilize locking spine devices in natural orifice procedures to locate tools at or near the abdominal walls such that the tools may be manipulated in a way that is intuitive to the surgeon given his/her experience with laparoscopic and/or open surgical techniques. Other systems that achieve this objective without the use of a locking spine are also useable and fall within the scope of this disclosure. One example is shown in FIG. 24 in which a system 400 may be attached to the interior of the abdominal wall using a screw 402, t-bar 404, inflatable balloon anchor, expandable braid, or similar device embedded in the facial layer of the stomach wall W. According to this embodiment, the system 400 includes features that support a procedural cammula 406 introduced into the peritoneal space via a natural orifice as described above. In the example shown, the procedural cannula 406 is passed through or engaged with a guide ring 408 that helps to orient the distal end 410 of the procedural cannula 406, and thus tools 412 passed through the procedural cannula 406, towards the treatment site. As another alternative embodiment, the system may use magnetism to support, retain and/or locate tools at the desired vantage point, such as near the inside of the abdominal wall. This embodiment might use cannulas having magnetic features within the body, and an external electromagnetic outside the body. Alternatively, the embodiment might employ a steel/iron plate outside the body and magnetic cannulas that are attracted to the steel/iron plate.

While certain embodiments have been described above, it should be understood that these embodiments are presented by way of example, and not limitation. While these systems provide convenient embodiments for carrying out this function, there are many other instruments or systems varying in form or detail that may alternatively be used within the scope of the present invention. This is especially true in light of technology and terms within the relevant art(s) that may be later developed. Moreover, the disclosed embodiments may be combined with one another in varying ways to produce additional embodiments.

Any and all patents, patent applications and printed publications referred to above are incorporated by reference, including those relied upon for purposes of priority.

We claim:

1. A surgical access system comprising:
   an elongate support proportioned for insertion into a body cavity;
   an expandable frame supported by the elongate support, the frame expandable to an expanded position; and
   first and second tool cannulas each having a deflectable distal portion, the first and second tool cannulas pivotally coupled to the expandable frame such that the deflectable distal portions are distal to the distalmost portion of the frame, and a third tool cannula coupled to the frame, the third tool cannula longitudinally slidable relative to the elongate support between a first position and a second position to expand the frame to the expanded position, each tool cannula having a lumen for receiving a tool for performing a procedure within the body cavity;
   wherein the frame includes at least two frame members, each frame member having a first end pivotally coupled to one of the first and second tool cannulas and a second end pivotally coupled to the third tool cannula.

2. The system of claim 1, wherein the elongate support includes a segmented spine formed of a plurality of spine elements coupled by a cable, the support moveable from a flexible position to a rigid position upon application of tension to the cable.

3. The system of claim 1, wherein the elongate support includes a lumen, and wherein the tool cannulas extend through the lumen.

4. The system of claim 1, wherein the first tool cannula includes a plurality of pull elements coupled to its distal portion, the distal portion deflectable in response to application of tension on at least one of the pull elements.

5. The system of claim 4, wherein the pull elements include proximal ends coupled to a gimbal, the gimbal moveable in multiple directions to apply tension to the pull elements.

6. The system of claim 5, wherein the gimbal includes a tool port having an opening, wherein the gimbal is moveable by movement of the tool port, and wherein the tool port is proportioned to receive a distal end of a tool as the distal end of the tool is advanced into the tool cannula.

7. The system of claim 6, wherein the tool port is moveable through movement of a handle of a tool positioned within the tool port.

8. The system of claim 4, wherein each of the tool cannulas includes a plurality of pull elements coupled to its distal portion and wherein the system further includes: a mount coupled to a proximal portion of the elongate support, and a pair of actuators on the mount, wherein the pull elements of each of the first and second tool cannula are coupled to a corresponding one of the actuators.

9. The system of claim 8, wherein each actuator includes an instrument port, such that a tool positioned in one of the tool cannulas extends through a corresponding one of the instruments ports, and wherein movement of a handle of a tool within the instrument port actuates the pull elements.

10. The system of claim 8, wherein the mount is attachable to a surgical table.

11. The system of claim 1, further including an access cannula insertable into a natural orifice and an anchor coupled to the access cannula and expandable to retain the access cannula within an incision formed within a wall of an internal body organ, the access cannula having a lumen, the elongate support, frame and tool cannulas insertable through the lumen of the access cannula when the frame is in a collapsed position.

12. A surgical access system comprising:
   an elongate support proportioned for insertion into a body cavity;
   an expandable frame supported by the elongate support, the frame expandable to an expanded position; and first and second tool cannulas each having a deflectable distal portion, the first and second tool cannulas coupled to the expandable frame such that the deflectable distal portions are distal to the distalmost portion of the frame, each tool cannula having a lumen for receiving a tool for performing a procedure within the body cavity;

wherein the frame includes at least two frame members, each frame member pivotally coupled to a tool cannula.

13. The system of claim 12, further including a sliding member longitudinally slidable relative to the first and second tool cannulas, wherein the at least two frame members are pivotally coupled to the sliding member such that longitudinal movement of the sliding member causes the at least two frame members to simultaneously pivot to expand the frame.

14. A method of performing a minimally invasive medical procedure, comprising the steps of:
inserting an elongate support through an incision into a body cavity, wherein the support includes a frame on its distal end and first, second, and third tool cannulas, the frame including at least two frame members, each having a first end pivotally coupled to the third tool cannula and a second end pivotally coupled to one of the first and second tool cannulas;
longitudinally sliding the third tool cannula relative to the first and second tool cannulas to pivot the frame members, expanding the frame within the body cavity;
positioning medical tools within the tool cannulas and performing a procedure within the body cavity using the medical tools; and
deflecting distal portions of the first and second tool cannulas to alter the positions of the medical tools extending through the tool cannulas into the body cavity, said distal portions positioned distally of the distalmost portion of the frame.

15. The method of claim 14, wherein deflecting a tool cannula includes applying tension to at least one of a plurality of pull elements coupled to the distal portion of the tool cannula.

16. The method of claim 15, wherein a proximal portion of the tool extends through a tool port, wherein the pull elements are coupled to the tool port, and wherein deflecting the tool cannula includes manipulating the proximal portion of the tool.

17. The method of claim 16, wherein the method includes adjusting an amount by which tool cannula deflection is amplified relative to corresponding movement of the tool.

18. The method of claim 14, further including the step of locking the tool cannula in a deflected position.

19. The method of claim 18, Further including the step of, with the tool cannula in the deflected position, withdrawing the tool from the tool cannula and inserting a second tool into the tool cannula.

20. The method of claim 14, wherein the method includes inserting the elongate support through a natural orifice selected from the group of natural orifices including the mouth, the vagina and the rectum and then advancing the elongate support through the incision.

21. The method of claim 14, wherein the method includes converting the elongate support from a flexible state to a rigid state within the body cavity, wherein in rigid state the support member assumes a curvature selected to orient the tool cannulas towards a target site within the body cavity.

22. The method of claim 21, wherein the incision is in the stomach, and wherein the curvature causes the support member to extend in anterior and superior directions from the incision.

23. The method of claim 21, wherein the incision is in the stomach, and wherein the curvature positions the tools in the tool cannulas for access to a gall bladder within the body cavity.

24. The method of claim 14, wherein expansion of the frame orients distal openings in the tool cannulas towards a target site within the body.

25. The method of claim 14 wherein expansion of the frame laterally moves the second tool cannula relative to the first tool cannula.

26. The method of claim 14 further including:
locking at least one of the tool cannulas in a deflected position.

* * * * *